(12) United States Patent
Sun et al.

(10) Patent No.: US 11,039,942 B2
(45) Date of Patent: Jun. 22, 2021

(54) DRUG ELUTING STENT AND METHOD OF USE OF THE SAME FOR ENABLING RESTORATION OF FUNCTIONAL ENDOTHELIAL CELL LAYERS

(71) Applicant: SINO MEDICAL SCIENCES TECHNOLOGY INC., Tianjin (CN)

(72) Inventors: Jianhua Sun, Tianjin (CN); Christophe Bureau, Tianjin (CN); Wenbin Cai, Tianjin (CN); Tianzhu Li, Tianjin (CN); Xiaoran Kang, Tianjin (CN)

(73) Assignee: SINO MEDICAL SCIENCES TECHNOLOGY INC., Tianjin (CN)

( * ) Notice: Subject to any disclaimer, the term of this patent is extended or adjusted under 35 U.S.C. 154(b) by 151 days.

(21) Appl. No.: 15/797,862

(22) Filed: Oct. 30, 2017

(65) Prior Publication Data
US 2018/0042738 A1    Feb. 15, 2018

Related U.S. Application Data

(63) Continuation-in-part of application No. 13/850,679, filed on Mar. 26, 2013, now Pat. No. 9,884,142.
(Continued)

(51) Int. Cl.
*A61F 2/24*    (2006.01)
*A61F 2/82*    (2013.01)
(Continued)

(52) U.S. Cl.
CPC .............. *A61F 2/82* (2013.01); *A61L 31/022* (2013.01); *A61L 31/06* (2013.01); *A61L 31/10* (2013.01);
(Continued)

(58) Field of Classification Search
CPC ......... A61L 2300/416; A61L 2300/608; A61L 2420/02; A61L 2420/06; A61L 31/148;
(Continued)

(56) References Cited

U.S. PATENT DOCUMENTS 6,120,904 A    9/2000   Hostettler et al.
7,063,884 B2 *  6/2006   Hossainy ................ A61L 31/10
                                                                428/212
(Continued)

FOREIGN PATENT DOCUMENTS

FR           2843757 B1    2/2004

OTHER PUBLICATIONS

Bhattacharya A. et al., "Grating: a versatile means to modify polymers techniques, factors and applications," Prog. Polym. Sci., 29:767-814 (2004).
(Continued)

*Primary Examiner* — Seema Mathew
(74) *Attorney, Agent, or Firm* — Arrigo, Lee, Guttman & Mouta-Bellum LLP

(57) ABSTRACT

The present disclosure relates to drug eluting stents, methods of making, using, and verifying long-term stability of the drug eluting stents, and methods for predicting long term stent efficacy and patient safety after implantation of a drug eluting stent. In one embodiment, a drug eluting stent may include a stent framework; a drug-containing layer; a drug embedded in the drug-containing layer; and a biocompatible base layer disposed over the stent framework and supporting the drug-containing layer. The drug-containing layer may have an uneven coating thickness. In addition or in alternative, the drug-containing layer may be configured to significantly dissolve/dissipate/disappear between 45 days and 60 days after stent implantation. Stents of the present disclosure may reduce, minimize, or eliminate patient risks associated
(Continued)

with the implantation of a stent, including, for example, restenosis, thrombosis, and/or MACE.

**8 Claims, 39 Drawing Sheets
(34 of 39 Drawing Sheet(s) Filed in Color)**

Related U.S. Application Data which is a continuation of application No. 11/808,926, filed on Jun. 13, 2007, now abandoned.

(60) Provisional application No. 60/812,990, filed on Jun. 13, 2006.

(51) Int. Cl.
*A61L 31/16* (2006.01)
*A61L 31/10* (2006.01)
*A61L 31/02* (2006.01)
*A61L 31/06* (2006.01)
*A61L 31/14* (2006.01)

(52) U.S. Cl.
CPC ............ *A61L 31/148* (2013.01); *A61L 31/16* (2013.01); *A61F 2250/0067* (2013.01); *A61L 2300/416* (2013.01); *A61L 2300/608* (2013.01); *A61L 2420/02* (2013.01); *A61L 2420/06* (2013.01)

(58) Field of Classification Search
CPC ...... A61L 31/16; A61L 2420/08; A61L 31/08; A61L 31/06; A61F 2250/0067; A61F 2/82; A61F 2/2419; A61F 2002/825; A61F 2/86; A61F 2/91; A61F 2/2415; A61F 2/24
See application file for complete search history.

(56) References Cited

U.S. PATENT DOCUMENTS

| | | | |
|---|---|---|---|
| 7,119,030 B2 * | 10/2006 | Bureau | C09D 5/4476 438/758 |
| 8,563,041 B2 | 10/2013 | Grayson et al. | |
| 9,056,153 B2 | 6/2015 | Chen et al. | |
| 9,863,052 B2 * | 1/2018 | Bureau | A61L 31/10 |
| 2002/0018795 A1 | 2/2002 | Whitbourne et al. | |
| 2002/0051730 A1 | 5/2002 | Bodnar et al. | |
| 2002/0065551 A1 | 5/2002 | Koole et al. | |
| 2003/0083646 A1 | 5/2003 | Sirhan et al. | |
| 2003/0088307 A1 * | 5/2003 | Shulze | A61F 2/91 623/1.15 |
| 2004/0053381 A1 | 3/2004 | Williams et al. | |
| 2004/0144655 A1 * | 7/2004 | Bertrand | C08F 289/00 205/235 |
| 2005/0125054 A1 | 6/2005 | Bhat et al. | |
| 2005/0255631 A1 * | 11/2005 | Bureau | C09D 5/4476 438/106 |
| 2005/0267565 A1 | 12/2005 | Dave et al. | |
| 2005/0287287 A1 * | 12/2005 | Parker | A61F 2/82 427/2.21 |
| 2006/0013853 A1 * | 1/2006 | Richard | A61L 31/10 424/423 |
| 2006/0136048 A1 * | 6/2006 | Pacetti | A61L 31/10 623/1.42 |
| 2006/0184226 A1 | 8/2006 | Austin | |
| 2006/0265043 A1 | 11/2006 | Mandrusov et al. | |
| 2007/0209943 A1 | 9/2007 | Bureau | |
| 2009/0076591 A1 * | 3/2009 | Girton | A61F 2/91 623/1.16 |
| 2010/0081992 A1 | 4/2010 | Ehrenreich et al. | |
| 2013/0236498 A1 * | 9/2013 | Mangiardi | A61K 31/436 424/400 |
| 2015/0174298 A1 | 6/2015 | Brouzes et al. | |
| 2016/0177109 A1 | 6/2016 | Hendricks et al. | |
| 2018/0042738 A1 * | 2/2018 | Sun | C08L 67/04 |

OTHER PUBLICATIONS

Geoghegan M., "Linear polymers in networks: swelling, diffusion, and interdigitation," Adv. in Solid State Phys., 45:29-44 (2005).
Maeda N. et al., "Adhesion and friction mechanisms of polymer-on-polymer surfaces," Science, 297:379-82 (2002).
Wkipedia entry for "adhesion" downloaded Jul. 3, 2011.
Non-Final Office Action for U.S. Appl. No. 11/808,926, dated Jan. 11, 2010, which is related to this subject application.
Non-Final Office Action for U.S. Appl. No. 11/808,926, dated Apr. 26, 2011, which is related to this subject application.
Non-Final Office Action for U.S. Appl. No. 13/850,679, dated Mar. 10, 2015, which is related to this subject application.
Non-Final Office Action for U.S. Appl. No. 13/850,679, dated Jul. 15, 2016, which is related to this subject application.
Non-Final Office Action for U.S. Appl. No. 13/850,679, dated Mar. 2, 2017, which is related to this subject application.
Notice of Allowance for U.S. Appl. No. 13/850,679, dated Oct. 11, 2017, which is related to this subject application.

* cited by examiner

45 Day Evans Blue
Evan's Blue Uptake Data

| Stent Type | Combined stent halves [Evan's Blue Uptake %] |
|---|---|
| BuMA Supreme N = 5 | 35.36 ± 15.91 |
| Xience N = 4 | 54.71 ± 1.74 |
| Synergy N = 5 | 42.84 ± 13.93 |
| Vision N = 4 | 11.2 ± 12.09 |

FIG. 12D

45 Day VE-cadherin
VE-Cadherin and P120 Immunofluorescence Staining

| Stent Type | Percentage of EC Barrier Protein Expression | | |
|---|---|---|---|
| | Above Struts | P Value | Between Struts |
| BuMA Supreme N=5 | 60.77 ± 34.46 | 0.014 | 59.35 ± 34.27 |
| Xience N=4 | 37.09 ± 21.88 | | 36.46 ± 20.7 |
| Synergy N=5 | 42.99 ± 23.75 | | 46.29 ± 24.39 |
| Vision N=4 | 97.81 ± 3.74 | | 98.07 ± 2.88 |

FIG. 13D

GROSS IMAGES OF EVAN'S BLUE UPTAKE

1313 Lt iliac – Xience
Percentage (%) of Evan's Blue positive area = 42.95

Assessment of Endothelial Barrier Function – Evan's Blue Uptake

Table 3. Mean percentage (%) of Evan's Blue positive area by visual examination from both stent halves, normalized to total stented area (90 days)

| Stent Type | Combined stent halves [Evan's Blue Uptake %] |
|---|---|
| BuMA Supreme N=6 | 22.89 ± 8.25 |
| Xience N=5 | 39.41 ± 12.5 |
| Synergy N=5 | 31.11 ± 20.62 |
| Vision N=6 | 6.6 ± 4.67 |

FIG. 14D

Dual IHC for Endothelial Coverage with Confocal Microscopy Analysis

Assessment Endothelial Cell Barrier Function by VE-cadherin and P120 Immunofluorescence Staining (90 days)

Table 3. Mean percentage (%) of Co-localized VE-cadherin and P120 immunofluorescence area (μm2) above and between struts relative to total stented area (μm2). Data collected from both halves of each stent

| Stent Type | Percentage of EC Barrier Protein Expression | |
|---|---|---|
| | Above Struts | Between Struts |
| aUMASupreme N=6 | 82.54 ± 20.76 | 81.56 ± 22.17 |
| Xience N=5 | 55.73 ± 24.32 | 56.38 ± 25.79 |
| Synergy N=5 | 80.73 ± 21.62 | 82.36 ± 20.08 |

FIG. 15D

DRUG ELUTING STENT AND METHOD OF USE OF THE SAME FOR ENABLING RESTORATION OF FUNCTIONAL ENDOTHELIAL CELL LAYERS

CROSS-REFERENCE TO RELATED APPLICATIONS

The present application is a continuation-in-part of U.S. patent application Ser. No. 13/850,679, filed Mar. 26, 2013, which is a continuation of U.S. patent application Ser. No. 11/808,926, filed Jun. 13, 2007, which claims benefit of priority to U.S. Provisional Patent Application No. 60/812,990, filed Jun. 13, 2006, the entire contents of which are all incorporated herein by reference.

TECHNICAL HELD

The present disclosure relates to drug eluting stents, methods of making and using the drug eluting stents, as well as methods for predicting long term stent efficacy and patient safety after implantation of a drug eluting stent. More specifically, and without the present disclosure relates to the design of a drug eluting stent comprising a stent framework (e.g., metal based or made with biodegradable materials) and a layer or layers covering all or part of the surface of said stent, capable of hosting a drug and releasing it in a sustained manner, in such a way that patient risks associated with the implantation of said drug eluting stent are minimized or eliminated. The stents disclosed herein are capable of enabling functional restoration of endothelial cell layers after implantation.

BACKGROUND

Over the years, the use of coatings for medical devices and drug delivery has become a necessity, notably for augmenting the capabilities of medical devices and implants. Drug eluting medical devices have emerged as a leading biomedical device for the treatment of cardiovascular disease.

Heart disease and heart failure are two of the most prevalent health conditions in the U.S. and the world. In coronary artery disease, the blood vessels in the heart become narrow. When this happens, the oxygen supply is reduced to the heart muscle. A primary treatment of coronary artery disease was initially done by surgery, e.g., CABG (Coronary Artery Bypass Graft), which are normal and efficient procedures performed by cardiac surgeons. The mortality and morbidity, however, were rather high.

In the 1960s, some physicians developed a less invasive treatment by using medical devices. These devices were inserted through a small incision at the femoral artery. For example, balloon angioplasty (which may be used to widen an artery that has become narrowed using a balloon catheter which is inflated to open the artery and is also termed PTCA (Percutaneous Transluminal Coronary Angioplasty)) is used in patients with coronary artery disease. Following balloon angioplasty, approximately 40 to 50% of coronaries arteries are generally affected by restenosis (the re-narrowing of a blood vessel after it has been opened, usually by balloon angioplasty), usually within 3 to 6 months due to either thrombosis (the development of a blood clot in the vessels which may clog a blood vessel and stop the flow of blood) or abnormal tissue growth. As a result, restenosis constitutes one of the major limitations to the effectiveness of PTCA.

The introduction of the bare metal stent (BMS) in the late 1980s, when used to keep coronary arteries expanded, partially alleviated this problem, as well as that of the dissections of arteries upon balloon inflation in the PTCA procedure.

The stent is a mesh tube mounted on a balloon catheter (e.g., a long thin flexible tube that can be inserted into the body). In this example, the stent is threaded to the heart. However, the BMS initially continued to be associated with a general restenosis rate of around 25% of patients affected 6 months after stent insertion. Usually, stent struts end up embedded by the arterial tissue in growth. This tissue is typically made of smooth muscle cells (SMCs), the proliferation of which may be provoked by the initial damaging of the artery upon stent apposition.

As depicted in FIG. 1, the whole inner surface of the vessel 100 is covered by "active" of functional ECs 101, i.e. endothelial cells spontaneously producing nitrogen oxide (NO), a small molecule acting as a signal to stop the proliferation of SMCs 103 underneath. This natural release of NO by ECs 101 takes place generally when ECs 101 are in immediate contact to one another, e.g., paving the inner surface of the artery by a continuous and closely packed film.

When a stent (or a balloon) is inflated inside vessel 150, stent struts in contact with the vessel walls will partly destroy the EC layer and injure the artery, e.g. at contact points 105a and 105b. The natural release of NO is thus—at least locally at contact points 105a and 105b—highly perturbed. This injury may trigger the proliferation of SMCs as a repair mechanism, e.g., SMCs 107a and 107b. The uncontrolled proliferation of SMCs may cause the re-closing of the vessel, or "re-stenosis." If, while SMCs 107a and 107b are proliferating, ECs 101 can also proliferate and eventually cover again the stent struts and SMCs 107a and 107b via a continuous film, then the NO release may be restored and the proliferation of SMC's may be stopped. Consequently, the risk of restenosis may be lessened (if not eliminated) and the situation may stabilize.

One of the biggest challenges of the interventional cardiology industry since the 1990s has been to first understand and then secure this "race" for complete EC coverage and restoring the EC layer functions. The endothelium is a monolayer of cells lining the inside of all blood and lymph vasculature. One important function of the endothelium is to regulate the movement of fluid, macromolecules, and white blood cells between the vasculatureand the interstitial tissue. This is mediated, in part, by the ability of endothelial cells to form strong cell-cell contacts by using a number of transmembrane junctional proteins, including VE-Cadherin and p120-catenin. Colocalization of the two proteins is an indication of a well-functioning endothelial cell layer.

Two strategies have been historically considered to restore an artery following stent implantation. One goal of most Drug Eluting Stents (DES) designs is to promote the proliferation of active endothelial cells (ECs) to accelerate their migration and eventual coverage of the surface of the stent. If these new ECs are active, e.g., form a continuous and close packed film, they usually spontaneously release NO and thereby hinder the proliferation of SMCs.

Another goal of most DES designs is to inhibit the proliferation of smooth muscle cells (SMCs). Generally, this has been targeted via the local release of an anti-proliferative agent (usually an anti-angiogenesis drug, similar to anti-cancer agents) from the surface of the stent.

Many DES on the market are made on the basis of a polymeric release matrix from which the drug is eluted. First and second generation stents were often coated with a biostable polymer. In such stents, the polymer stays permanently on the stent, and is generally assumed to have little effect both on the inflammatory response and the proliferation of ECs. In some cases, however, these stents do not release 100% of the drug that their coating is hosting. In particular, sometimes the majority of the drug remains in the polymer coating for long periods of time. Furthermore, most drugs used so far are not selective and tend to inhibit the proliferation of ECs more than that of SMCs.

This drawback may have dramatic and potentially lethal consequences for the patients and, thus, for the DES industry. Indeed, despite the possible reduction in restenosis from ca. 20% with Bare Metal Stents (BMS) to ca. 5% with Drug Eluting Stents (DES) in the first year, the massive introduction of DES brought two new challenges: (1) the phenomenon of late thrombosis, i.e., re-clotting of the artery one year or more after stent implantation, and (2) progressive growth of the neo-intimal layer leading to restenosis again. Accordingly, what DES has generally accomplished is to delay the occurrence of restenosis yet cause other complications, such as thrombosis, in the years after the DES implantation.

The implantation of bare metal stents is understood to be a source of thrombosis, in addition to restenosis, but the former is generally handled by a systemic Dual Anti-Platelet Therapy (DAPT) associating two anti-thrombotic agents, e.g., aspirin and clopidogrel. For example, patients in whom a stent was implanted were often prescribed such DAPT for 1 to 2 months. With drug eluting stents, numerous cases of re-clotting of the artery due to coagulation (thrombosis) after interruption of the DAPT have been reported. Accordingly, many cardiologists maintain the DAFT for 3, 6, 9 and now 12 months or more. By 2005-2006, several cases were reported that myocardial infarction with total stent thrombosis may occur only a couple of weeks after interruption of an 18-month DAPT.

Late thrombosis is an abrupt complication which can be lethal when occurring if the patient is not under medical follow-up or—even if the patient is—while the patient is away from the cathlab or from an adequately equipped medical centre. Moreover, DAPT may present a bottleneck that is difficult to manage, as some patients may decide by themselves to stop it after a period of use, or forget to have their medicines refilled or to take their medicines, or may have to undergo a clinical intervention which could not be anticipated, and are thus in the position to have to stop the anti-thrombotic treatment.

The exact causes of late thrombosis still are not fully understood. Pathologists estimate that late thrombosis reveals an incomplete coverage of the stent by ECs, leaving metallic or polymeric materials in contact with the blood over prolonged periods, on which platelet adhesion is likely to occur, which may lead to catastrophic precipitation of a thrombus. Alternative interpretations propose that the incomplete coverage by ECs may be the result of the incomplete release of the drug from the release layer, which may inhibit the proliferation of ECs in their attempt to migrate and cover the surface of said polymer+drug+SMC layer.

The thickness of the stent struts may further present a source of hindrance of the proliferation of ECs. Whenever ECs have to proliferate on a surface, the rate of their proliferation is often negatively (and largely) influenced by the height of obstacles that they have to overcome on this surface towards complete coverage. Accordingly, not all stent designs and drug release profiles are equal. For example, when the DES is apposed in the artery, the injured EC layer has to overcome obstacles with a height roughly equal to the thickness of the stent strut+the thickness of the drug release polymer layer+the thickness of the SMC layer which has started to form. The former two thicknesses are related to the design of the DES, while the latter thickness is linked to the efficacy of the drug, its loading in the release layer, and its release rate. Thus a need still exists for developing a new stent and method of making a stent that can decrease patient risks associated with the implantation of stents (e.g., restenosis, thrombosis, MACE).

SUMMARY

The present disclosure relates to drug eluting stents, as well as methods of making and using the drug eluting stents, and a method of predicting stent efficacy and patient safety. In one embodiment, the drug eluting stent (1) combines four parts: a stent framework (2), a drug-containing layer (3), a drug (4), and a biocompatible base layer supporting the drug-containing layer (5). In one embodiment, the stent and the method of making the stent are designed so as to manipulate the time to achieve a sufficient re-endothelialization of the stent surface/vascular wall and improve endothelium function restoration by manipulating the thickness of the drug-containing layer and the distribution of that thickness. In one embodiment, the thickness of the drug-containing layer in the luminal side is different from the thickness in the abluminal side. In one embodiment, the stent minimizes late thrombosis, i.e. re-clotting of the artery one year or more after stent implantation and progressive thickness of the neo-intimal layer leading to restenosis again. In one embodiment, the stent and the method of making the stent are such that they reduce the number or frequency of major adverse cardiac events (MACE). In one embodiment, neointimal coverage or re-endothelialization of the surface of stent struts within 90 days significantly improves strength efficacy and patient safety.

A stent framework (2) may be fabricated from a single (or more) pieces of metal or wire or tubing. For example, the stent framework may comprise cobalt-chromium (e.g., MP35N or MP20N alloys), stainless steel (e.g., 316L), nitinol, tantalum, platinum, titanium, suitable biocompatible alloys, other suitable biocompatible materials, and/or combinations thereof.

In some embodiments, the stent framework (2) may be biodegradable. For example, the sent framework (2) may be fabricated from magnesium alloy, polylactic acid, polycarbonate polymers, salicylic acid polymers, and/or combinations thereof. In other words, any biocompatible but also biodegradable materials which can be fabricated in such way that the radical force is sufficient strong to be implantable and support to stabilize the lesion and vessel retraction, but where the thickness of the stent is less than 120 um.

In other embodiments, the stent framework (2) may be fabricated from one or more plastics, for example, polyurethane, teflon, polyethylene, or the like.

A drug-containing layer (3) may be made from polymers and may comprise a layer or layers covering all or part of the stent surface. Furthermore, a drug-containing layer (3) may be capable of hosting drug (4) and releasing the drug (4) in a sustained manner.

In one embodiment, the drug-containing layer may have an uneven coating thickness. For example, a thickness of the drug-containing layer on a luminal side of the stent and a thickness of the drug-containing layer on a lateral side of the stent is less than a thickness of the drug-containing layer on an abluminal side of the stent.

In one embodiment, for example on account of the uneven coating thickness, the drug-containing layer may release the drug within 30 days of implantation within a vessel. The release time may be verified, for example, using a standard animal PK study. Accordingly, when the drug eluting stent (1) is implanted into the human body vessel, the drug (4) may be released from coating (3) within 30 days or less. In other embodiments, the drug is released at different rates, such as 45 days or less, 60 days or less, 90 days or less, 120 days or less.

In some embodiments, the drug may be included only on an abluminal side of the stent.

In embodiments where the drug-containing layer (3) is made from a bio-degradable or bio-absorbable polymer/s, the polymer(s) may be bio-degraded or bio-absorbed between 45 days and 60 days of implantation of the stent. In other embodiments, the polymer/polymers is/are bio-degraded or bio-absorbed within, such as 45 days or less, 60 days or less, 90 days or less, 120 days or less.

In some embodiments, the polymer on a luminal side and/or a lateral side of the stent may differ from the polymer on an abluminal side. For example, one or more polymers forming the drug-containing layer on a luminal side of the stent and the drug-containing layer on a lateral side of the stent degrade faster than one or more polymers forming the drug-containing layers on an abluminal side of the stent.

The biocompatible base layer (5) may be formed over the stent framework (2) and may have a more biocompatible surface than the stent framework (2). For example, the biocompatible base layer (5) may be made from poly n-butyl methacrylate, PTFE, PVDF-HFP, poly(styrene-b-isobutylene-b-styrene), Parylene C, PVP, PEVA, SBS, PC, TiO2 or any material that has good biocompatibility (or combinations thereof).

Additional exemplary embodiments of this disclosure are provided below and numbered for reference purposes only:
1. A drug eluting stent, comprising:
   a stent framework;
   a drug-containing layer;
   a drug embedded in the drug-containing layer; and
   a biocompatible base layer disposed over the stent framework and supporting the drug-containing layer,
   wherein the drug-containing layer has an uneven coating thickness, optionally,
   wherein the drug-containing layer is configured to completely dissolve/between 45 days and 60 days after implantation of the drug eluting stent.
2. The drug eluting stent of embodiment 1, wherein the drug-containing layer is configured to release the drug within 30 days of implantation within a vessel.
3. The drug eluting stent of embodiment 1, wherein a thickness of the drug-containing layer on a luminal side of the stent and a thickness of the drug-containing layer on a lateral side of the stent is less than a thickness of the drug-containing layer on an abluminal side of the stent.
4. The drug eluting stent of embodiment 3, where a ratio between the thickness of the drug-containing layer on the luminal side and the thickness of the drug-containing layer on the abluminal side is between 2:3 and 1:7.
5. The drug eluting stent of embodiment 3 or 4, where a ratio between the thickness of the drug-containing layer on the lateral side and the thickness of the drug-containing layer on the abluminal side is between 2:3 and 1:7.
6. The drug eluting stent of any one of embodiments 1 through 5, wherein the drug is embedded only on the drug-containing layer on an abluminal side of the stent.
7. The drug eluting stent of any one of embodiments 1 through 6, wherein the stent framework is fabricated from a single piece of metal, wire, or tubing.
8. The drug eluting stent of embodiment 7, wherein the metal comprises at least one of stainless steel, nitinol, tantalum, cobalt-chromium MP35N or MP20N alloys, platinum, and titanium.
9. The drug eluting stent of any one of embodiments 1 through 6, wherein the stent framework is fabricated from a biodegradable material.
10. The drug eluting stent of any one of embodiments 1 through 9, wherein the drug comprises at least one of an antithrombogenic agent, an anticoagulant, an antiplatelet agent, an antineoplastic agent, an antiproliferative agent, an antibiotic, an anti-inflammatory agent, a gene therapy agent, a recombinant DNA product, a recombinant RNA product, a collagen, a collagen derivative, a protein analog, a saccharide, a saccharide derivative, an inhibitor of smooth muscle cell proliferation, a promoter of endothelial cell migration, proliferation, and/or survival, and combinations of the same.
11. The drug eluting stent of embodiment 10, wherein the drug comprises sirolimus and/or a derivative or analog.
12. The drug eluting stent of embodiment 1, wherein the drug-containing layer has a thickness between 5 and 12 µm.
13. The drug eluting stent of embodiment 1, wherein the drug-containing layer is selected from the group consisting of poly(hydroxyalkanoates) (PHAs), poly(ester amides) (PEAs), poly(hydroxyalkanoate-co-ester amides), polyacrylates, polymethacrylates, polycaprolactones, poly(ethylene glycol)(PEG), poly(propylene glycol) (PPG), poly(propylene oxide) (PPO), poly(propylene fumarate) (PPF), poly(D-lactide), poly(L-lactide), poly (D,L-lactide), poly(meso-lactide), poly(L-lactide-co-meso-lactide), poly(D-lactide-co-meso-lactide), poly(D,L-lactide-co-meso-lactide), poly(D,L-lactide-co-PEG), poly(D,L-lactide-co-trimethylene carbonate), poly(lactide-co-glycolide), poly(glycolic acid-co-trimethylene carbonate), poly(trimethylene carbonate), PHA-PEG, PBT-PEG (PolyActive®), PEG-PPO-PEG(Pluronic®), and PPF-co-PEG, polycaprolactones, polyglycerol sebacate, polycarbonates, biopolyesters, polyethylene oxide, polybutylene terephalate, polydioxanones, hybrids, composites, collagen matrices with grouth modulators, proteoglycans, glycosaminoglycans, vacuum formed small intestinal submucosa, fibers, chitin, dexran and mixtures thereof.
14. The drug eluting stent of embodiment 13, wherein the drug-containing layer is selected from tyrosine derived polycarbonates.
15. The drug eluting stent of embodiment 13, wherein the drug-containing layer is selected from poly(β-hydroxyalcanoate)s and derivatives thereof.
16. The drug eluting stent of embodiment 13, wherein the drug-containing layer comprises a polylactide-co-glycolide 50/50 (PLGA).
17. The drug eluting stent of embodiment 1, wherein the biocompatible base layer comprises at least one of poly n-butyl methacrylate, PTFE, PVDF-HFP, poly(styrene-b-isobutylene-b-styrene), Parylene C, PVP, PEVA, SBS, PC, or TiO2.

18. The drug eluting stent of embodiment 1, wherein the biocompatible base layer comprises an electro-grafted polymeric layer having an interdigitated surface with the drug-containing layer.
19. The drug eluting stent of embodiment 18, wherein the electro-grafted polymeric layer has a thickness between 10 nm and 1000 nm.
20. The drug eluting stent of embodiment 18, wherein the electro-grafted polymeric layer comprises a monomer selected from the group consisting of vinylics, epoxides, and cyclic monomers undergoing ring opening polymerization and aryl diazonium salts.
21. The drug eluting stent of embodiment 24, wherein the monomer is further selected from the group consisting of butyl methacrylate, methyl methacrylate, hydroxyethyl methacrylate, epsilon caprolactone, and 4-aminophenyl diazonium tetrafluoro borate.
22. A drug eluting stent, comprising:
    a stent framework;
    a biodegradable drug-containing layer;
    a drug embedded in the drug-containing layer; and
    a biocompatible base layer disposed over the stent framework and supporting the drug-containing layer,
    wherein the drug-containing layer is configured to significantly dissolve between 45 days and 60 days after implantation of the drug eluting stent.
23. The drug eluting stent of embodiment 22, wherein the drug-containing layer is formed from a plurality of polymers.
24. The drug eluting stent of embodiment 23, wherein one or more polymers forming the drug-containing layer on a luminal side of the stent and the drug-containing layer on a lateral side of the stent degrade faster than one or more polymers forming the drug-containing layers on an abluminal side of the stent.
25. The drug eluting stent of embodiment 22, wherein the stent framework is fabricated from a single piece of metal, wire, or tubing.
26. The drug eluting stent of embodiment 25, wherein the metal comprises at least one of stainless steel, nitinol, tantalum, cobalt-chromium MP35N or MP20N alloys, platinum, and titanium.
27. The drug eluting stent of embodiment 23, wherein the stent framework is fabricated from a biodegradable material.
28. The drug eluting stent of embodiment 22, wherein the drug comprises at least one of an antithrombogenic agent, an anticoagulant, an antiplatelet agent, an antineoplastic agent, an antiproliferative agent, an antibiotic, an antiinflammatory agent, a gene therapy agent, a recombinant DNA product, a recombinant RNA product, a collagen, a collagen derivative, a protein analog, a saccharide, a saccharide derivative, an inhibitor of smooth muscle cell proliferation, a promoter of endothelial cell migration, proliferation, and/or survival, and combinations of the same.
29. The drug eluting stent of embodiment 22, wherein the drug comprises sirolimus and/or a derivative or analog.
30. The drug eluting stent of embodiment 22, wherein the drug-containing layer has a thickness between 5 and 12 μm.
31. The drug eluting stent of embodiment 22, wherein the drug-containing layer is selected from the group consisting of poly(hydroxyalkanoates) (PHAs), poly(ester amides) (PEAs), poly(hydroxyalkanoate-co-ester amides), polyacrylates, polymethacrylates, polycaprolactones, poly(ethylene glycol)(PEG), poly(propylene glycol)(PPG), poly(propylene oxide) (PPO), poly(propylene fumarate) (PPF), poly(D-lactide), poly(L-lactide), poly (D,L-lactide), poly(meso-lactide), poly(L-lactide-co-meso-lactide), poly(D-lactide-co-meso-lactide), poly(D,L-lactide-co-meso-lactide), poly(D,L-lactide-co-PEG), poly(D,L-lactide-co-trimethylene carbonate), poly(lactide-co-glycolide), poly(glycolic acid-co-trimethylene carbonate), poly(trimethylene carbonate), PHA-PEG, PBT-PEG (PolyActive®), PEG-PPO-PEG(Pluronic®), and PPF-co-PEG, polycaprolactones, polyglycerol sebacate, polycarbonates, biopolyesters, polyethylene oxide, polybutylene terephalate, polydioxanones, hybrids, composites, collagen matrices with grouth modulators, proteoglycans, glycosaminoglycans, vacuum formed small intestinal submucosa, fibers, chitin, dexran and mixtures thereof.
32. The drug eluting stent of embodiment 31, wherein the drug-containing layer is selected from tyrosine derived polycarbonates.
33. The drug eluting stent of embodiment 31, wherein the drug-containing layer is selected from poly(β-hydroxyalcanoate)s and derivatives thereof.
34. The drug eluting stent of embodiment 31, wherein the drug-containing layer comprises a polylactide-co-glycolide 50/50 (PLGA).
35. The drug eluting stent of embodiment 22, wherein the biocompatible base layer comprises at least one of poly n-butyl methacrylate, PTFE, PVDF-HFP, poly(styrene-b-isobutylene-b-styrene), Parylene C, PVP, PEVA, SBS, PC, or TiO2.
36. The drug eluting stent of embodiment 22, wherein the biocompatible base layer comprises an electro-grafted polymeric layer having an interdigitated surface with the drug-containing layer.
37. The drug eluting stent of embodiment 36, wherein the electro-grafted polymeric layer as a thickness between 10 nm and 1000 nm.
38. The drug eluting stent of embodiment 36, wherein the electro-grafted polymeric layer comprises a monomer selected from the group consisting of vinylics, epoxides, and cyclic monomers undergoing ring opening polymerization and aryl diazonium salts.
39. The drug eluting stent of embodiment 38, wherein the monomer is further selected from the group consisting of butyl methacrylate, methyl methacrylate, hydroxyethyl methacrylate, epsilon caprolactone, and 4-aminophenyl diazonium tetrafluoro borate.
40. A method of using the stent according to any one of embodiments 1 through 39, the method comprising implanting the stent into a subject for the treatment of angiostenosis or to prevent restenosis, thrombosis, tumor growth, angioma or, obstruction of lacrimal gland.
41. The method of embodiment 40, wherein the stent is implanted into a vessel.
42. The method of embodiment 41, wherein the vessel is the left main coronary artery, circumflex artery, left anterior descending coronary artery, an iliac vessel, a carotid artery, or a neurovascular vessel.
43. A method of treatment, comprising: a step of delivering the stent according to any one of embodiments 1 through 39 into a lumen; a step of radially expanding the stent within the lumen; and a step of eluting a drug from a drug coating layer in the surface of the stent allowing the drug to act on the lumen and/or albumen surface.

44. A method of reducing, minimizing, or eliminating patient risks associated with the implantation of a stent by using any one of the stents according to any one of embodiments 1 through 39.
45. A method of fabricating a drug eluting stent, the method comprising:
providing a stent framework; and
unevenly coating the stent framework with at least one polymer mixed with at least one drug.
46. The method of embodiment 45, herein unevenly coating comprises coating the luminal and/or lateral sides of the stent with a thinner coating than the coating of the abluminal side, preferably wherein the coating that is thinner is a drug-containing layer and/or a biocompatible base layer underneath the drug-containing layer.
47. The method of embodiment 45, further comprising dissolving at least one polymer and at least one drug to form the at least one polymer mixed with at least one drug.
48. The method of embodiment 45, wherein unevenly coating the stent framework comprises spray coating the stent framework with the at least one polymer mixed with at least one drug.
49. The method of embodiment 46, wherein unevenly coating the stent framework comprises rotating the stent framework during spray coating to generate a centrifugal force.
50. The method of embodiment 49, wherein the centrifugal force causes a greater thickness of the mixture on an abluminal side of stent framework with respect to a luminal side of the stent framework and a lateral side of the stent framework.
51. The method of embodiment 45, further comprising drying the coated stent framework in a vacuum oven.
52. The method of embodiment 51, wherein the coated stent framework is dried between 40° C. to 50° C.
53. The method of embodiment 48, wherein a flow of the spray is 24 μL/s or less
54. The method of embodiment 48, wherein a volume of the spray is 192 μL/s or less.
55. The method of embodiment 48, wherein the spray coating is performed at 0.3 bars pressure or less.
56. The method of embodiment 49, wherein a speed of the rotation of the stent is at least 2000 rpm.
57. The method of embodiment 48, wherein a distance between a nozzle performing the spray coating and the stent framework is 6.5 mm or less.
58. The method of any of embodiments 45 to 57, further comprising:
electro-grafting at least one polymer onto the stent framework before spray coating the mounted framework.
59. The method of embodiment 58, further comprising:
baking the electro-grafted polymer at room temperature or higher before spray coating the mounted framework.
60. The method of embodiment 59, wherein the baking is performed in atmosphere conditions.
61. The method of embodiment 59, wherein the baking is performed in nitrogen.
62. The method of embodiment 59, wherein the baking is performed in vacuum.
63. A method of verifying long-term efficacy and safety of a stent in human through implantation into a rabbit animal model, the method comprising:
imaging the stent implanted into a rabbit model with at least one of a scan electron microscope (SEM) or an Evans Blue uptake between 90 days and 120 days after implantation to verify that an endothelial layer of the vessel covers at least 90% of a surface of the stent, and that the Evans blue uptake of the endothelium covering the stent is less than 30%.
64. A method of reducing and/or eliminating the restenosis, thrombosis or MACE of a blood vessel associated with the stent implantation, comprising the steps of
a) suppressing the smooth muscle cell proliferation of the blood vessel after the stent implantation within the first 30 days of the stent implantation; and
b) achieving sufficient re-endothelialization of the blood vessel within 3 months of the stent implantation such that endothelium function restoration can be achieved within 12 months of the stent implantation.
65. The method of embodiment 64, wherein the vessel is a blood vasculature vessel.
66. The method of embodiment 64, wherein the step of suppressing the smooth muscle proliferation is achieved by controlled release of a suitable drug from the implanted stent through proper dosage and release curve.
67. The method of embodiment 66, wherein the drug is completely released by 30 days after the stent implantation.
68. The method of embodiment 64, wherein the implanted stent has a layer of biocompatible and biodegradable carrier materials to promote the complete drug release within 30 days of implantation.
69. The method of embodiment 64, wherein the biocompatible and biodegradable carrier material is PLGA or PLA.
70. The method of embodiment 68, wherein the drug carrier layer is completely disappeared within 60 days of implantation.
71. The method of embodiment 67, wherein the surface of the implanted stent is smooth, or without significant obstacles for the endothelial cell to grow upon, to reestablish the proper interaction among the cells and to cover the stent strut surface.
72. The method of embodiment 66, wherein the surface of the stent is coated with polymer using electro- or chemical grafting coating technology.
73. The method of embodiment 66, wherein the stent has a thickness of about 80 um to 110 um.
74. The method of embodiment 73, wherein the stent thickness is about 100 to 110 um.
75. The method of embodiment 68, wherein the suitable drug is selected from a group consisting of sirolimus, paclitaxel, everolimus, biolimus, novolimus, tacrolimus, pimecrolimus and zotarolimus.
76. The method of embodiment 66, wherein the suitable stent can be a metal stent, or a biodegradable stent.
77. The method of embodiment 66 wherein the suitable stent is a polymeric stent, partially or completely biodegradable.
78. A method of predicting long term stent efficacy and patient safety after implantation of a drug eluting stent, the method comprising assessing the percentage of functional restoration of the endothelium coverage of the stent and/or blood vessel after stent implantation in an animal model, wherein about complete re-endothelialization at about 90 days post-stent implantation is predictive of long term stent efficacy and patient safety after stent implantation. For example, the assessment may include using an animal model to assess the percentage of the coverage, a thickness and permeability of the endothelial layer and a structure of the endothelial layer. The structure may include the type of tissue, for example, the tissue composition in terms of smooth muscle cells, matrix, and endothelial cells.

79. The method of embodiment 78, wherein long term stent efficacy comprises absence of significant restenosis of the vessel at the area of stent implantation.
80. The method of embodiment 78, wherein patient safety comprises absence of thrombosis of the vessel within 1 year post-stent implantation. In some embodiments, the thrombosis may be absent at 5 years post-stent implantation.
81. The method of embodiment 78, wherein patient safety comprises significant absence of MACE within 1 year post-stent implantation. In some embodiments, the absence of MACE may be at 5 years post-stent implantation.
82. The stent or the method according to any one of embodiments 1 through 81, wherein the uneven thickness of the drug-containing layer is achieved by spray coating of the drug-containing layer.
83. The stent or the method according to any one of embodiments 1 through 81, wherein the thinner portion of the drug-containing layer releases the drug faster than the thicker portion of the drug-containing layer, preferably within 10 to 20 days, wherein about complete release of the drug from the drug-containing layer occurs within 30 days of stent implantation.
84. Use of the stent according to any one of embodiments 1 to 39 in the manufacture of a medicament or a device for treating or preventing a vascular disease, preferably angiostenosis or to prevent restenosis, thrombosis, tumor growth, angioma or obstruction of lacrimal gland.
85. The stent or the method according to any one of embodiments 1 to 83, wherein the stent framework comprises an 8 crest design.
86. The stent or the method according to any one of embodiments 1 to 83, wherein the stent framework comprises a 10 crest design.
87. The stent or the method according to any one of embodiments 1 to 83, wherein the stent framework comprises an 11 crest design.
88. The stent or the method according to any e of embodiments 1 to 83, wherein the stent framework comprises a plurality of stent poles having a wave design.
89. The stent or the method according to any one of embodiments 1 to 83, wherein the stent framework comprises a plurality of single linking poles alternating between two linking poles and three linking poles between stent poles in an axial direction.
90. The stent or the method according to any one of embodiments 1 to 83, wherein the stent framework comprises four linking poles on a first end in an axial direction and comprises four linking poles on a second end in the axial direction,
91. The stent or the method according to any one of embodiments 1 to 83, wherein a width of a crown is greater than a width of a pole.
92. The stent according to any one of embodiments 1-39 and 85-91, wherein the stent is a non-stainless steel stent.
93. The stent according to embodiment 92, wherein the stent comprises a cobalt-chromium alloy.
94. The method according to embodiment 46, wherein the coating is designed for the thinner layer to release at least one drug from the drug-containing layer faster than from the thicker layer, preferably within 10-20 days, more preferably wherein about complete release is achieved within 30 days of stent implantation.
95. The method according to embodiment 94, wherein the drug-containing layer comprises a drug or drugs that suppress smooth muscle cell proliferation and/or promote endothelial cell migration, proliferation, and/or survival after stent implantation, preferably sirolimus.
96. The method according to embodiment 94, wherein the coating is designed to promote functional re-endothelialization of the stent within months of the stent implantation such that endothelium function restoration can be achieved within 12 months of the stent implantation.
97. The method according to embodiment 94, wherein the coating is designed to completely dissolve between 45 days and 60 days of implantation.
98. The method according to any one of embodiments 46 and 94-98, wherein the drug-containing layer comprises PLGA and the biocompatible base layer, when present, comprises PBMA.
99. The method according to embodiment 78, wherein the percentage of functional restoration of the endothelium coverage of the stent and/or blood vessel in the patient is reasonably predictable from a study in an animal model, preferably a rabbit animal model.
100. The method according to embodiment 78 or 79, wherein the percentage of functional restoration of the endothelium coverage of the stent is assessed by SEM, Evan's Blue staining, OCT, VE-Cadherin/P120 confocal staining colocalization, or a combination of the same.
101. The method according to embodiment 78, wherein the stent is implanted into a heart vessel.
102. The method according to embodiment 78 or 79, wherein the stent is a stainless steel stent.
103. The method according to embodiment 78 or 79, wherein the stent is a non-stainless steel stent.
104. The method according to embodiment 78 or 79, wherein the stent comprises a cobalt-chromium alloy.
105. The method according to any one of embodiments 78-89 and 99-104, wherein the stent is a drug-eluting stent.
106. The method according to embodiment 105, wherein the drug-eluting stent comprises a drug or drugs that suppress smooth muscle cell proliferation and/or promote endothelial cell migration, proliferation, and/or survival after stent implantation, preferably sirolimus.
107. The method according to embodiment 105, wherein the stent is selected from any one of the stents according to any one of embodiments 1-39 and 84-93.

BRIEF DESCRIPTION OF THE FIGURES

The drawings depict only example embodiments of the present disclosure and do not therefore limit its scope. They serve to add specificity and detail.

The patent or application file contains at least one drawing executed in color. Copies of this patent or patent application publication with color drawings will be provided by the Office upon request and payment of the necessary fee.

FIG. 12D is a table summarizing the results of Evan's Blue update data at 45 day from experiments done with a stent according to embodiments of the present disclosure (BuMA Supreme) and not according to the present disclosure (Xience and Synergy).

FIG. 13D is a table summarizing the results of the VE-Cadherin/P120 colocalization data at 45 days from experiments done with a stent according to embodiments of the present disclosure (BuMA Supreme) and not according to the present disclosure (Xience and Synergy).

FIG. 14D is a table summarizing the results of Evan's Blue update data at 90 days from experiments done with a stent according to embodiments of the present disclosure (BuMA Supreme) and not according to the present disclosure (Xience and Synergy).

FIG. 15D is a table summarizing the results of the VE-Cadherin/P120 colocalization data at 90 days from experiments done with a stem according to embodiments of the present disclosure (BuMA Supreme) and not according to the present disclosure (Xience and Synergy).

DETAILED DESCRIPTION

Figure 1A:
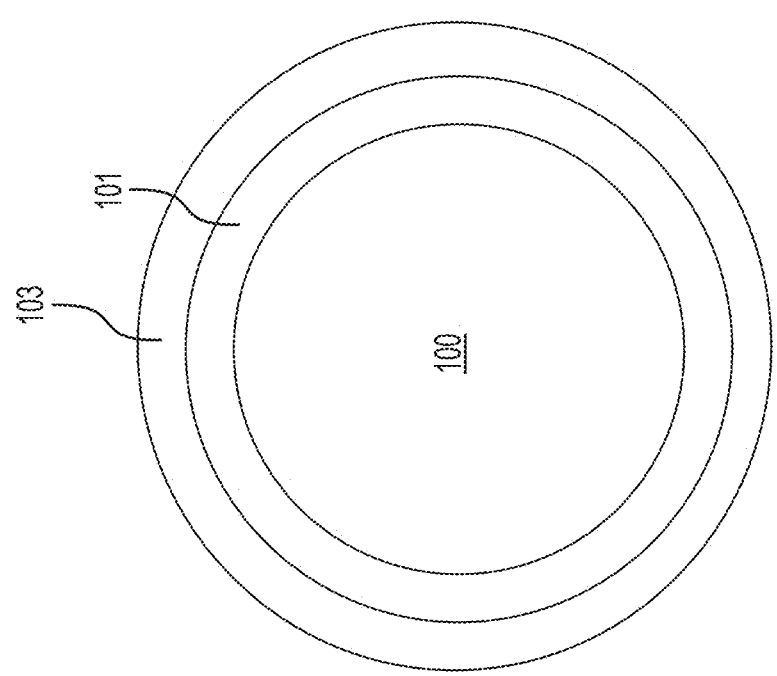
FIG. 1A depicts a vessel 100 prior to implantation of a stent.
Figure 1B:
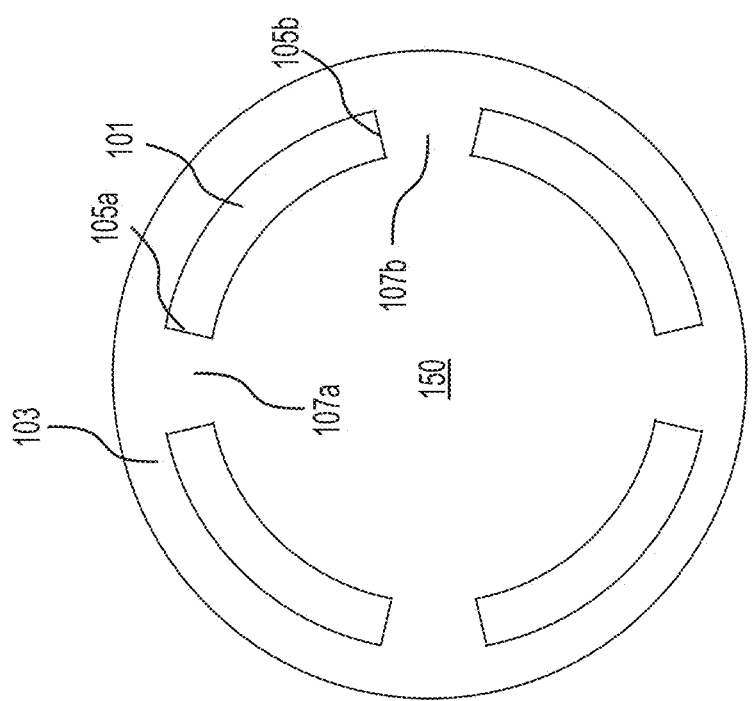
FIG. 1B depicts a vessel 150 after implantation of a stent.

The present disclosure relates to drug eluting stents, methods of making and using the drug eluting stents, as well as methods for predicting long term stent efficacy and patient safety after implantation of a drug-eluting stent. According to some embodiments of the present disclosure, the drug eluting stent (1) comprises four parts: a stent framework (2), a drug-containing layer (3), a drug (4), and a biocompatible base layer (5). In one embodiment, the stent may be made with stainless steel. In another embodiment, the stent may be made of CoCr alloy. In one embodiment, the stent has a between 80-120 um. The drug-containing layer may be formed of PLGA, and the biocompatible base layer may be formed of PBMA. The biocompatible base layer may be formed using an electrografting process.

The Stent Framework:

Stents are typically composed of a scaffold or scaffolding that includes a pattern or network of interconnecting structural elements or struts, formed from wires, tubes, or sheets of material rolled into a cylindrical shape. This scaffold gets its name because it physically holds open and, if desired, expands the wall of a passageway in a patient. Typically, stents are capable of being compressed or crimped onto a catheter so that they can be delivered to and deployed at a treatment site. Delivery includes inserting the stent through small lumens using a catheter and transporting it to the treatment site. Deployment includes expanding the stent to a larger diameter once it is at the desired location.

A stent framework (2) may be fabricated from a single (or more) piece(s) of metal or wire or tubing, including the 3D printing and laser cutting (e.g., starting from a wire). For example, the stent framework may be non-stainless steel or comprise stainless steel, nitinol, tantalum, cobalt-chromium (e.g., MP35N or MP20N alloys), platinum, titanium, suitable biocompatible alloys, other suitable biocompatible materials, and/or combinations thereof. In some embodiments, the stent is a non-stainless steel stent. In other embodiments, the stent framework may be fabricated from a metallic material or an alloy such as, but not limited to, cobalt chromium alloy (ELGILOY), stainless steel (316L), high nitrogen stainless steel, e.g., BIODUR 108, cobalt chrome alloy L-605, ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

In other embodiments, the stent framework (2) may be fabricated from one or more plastics, for example, polyurethane, teflon, polyethylene, or the like. In such embodiments, the stent framework (2) may be fabricated, for example, using 3-D printing.

The stent framework (2) may form a mesh. Accordingly, the stent framework (2) may expand upon implantation, either from external forces such as from a balloon catheter and/or from internal forces such as expansion of the mesh caused by increased temperature within the vessel. Upon expansion, the stent framework (2) may hold the vessel open.

In some embodiments, the stent framework (2) may be biodegradable. In order to effect healing of a diseased blood vessel, the presence of the stent is necessary only for a limited period of time, as the artery undergoes physiological remodeling over time after deployment. The development of a bioabsorbable stent or scaffold could obviate the permanent metal implant in the vessel, allow late expansive luminal and vessel remodeling, and leave only healed native vessel tissue after the full resorption of the scaffold. Stents fabricated from bioresorbable, biodegradable, bioabsorbable, and/or bioerodable materials such as bioabsorbable polymers can be designed to completely absorb only after or some time after the clinical need for them has ended. Consequently, a fully bioabsorbable stent can reduce or eliminate the risk of potential long-term complications and of late thrombosis, facilitate non-invasive diagnostic MRI/CT imaging, allow restoration of normal vasomotion, and provide the potential for plaque regression. For example, the sent framework (2) may be fabricated from chitosan, magnesium alloy, polylactic acid, polycarbonate polymers, salicylic acid polymers, and/or combinations thereof. Advantageously, a biodegradable stent framework (2) may allow for the vessel to return to normalcy after a blockage has been cleared and flow restored by the stent (1). The term "biodegradable" as used herein is interchangeable with the terms "bioabsorbable" or "bioerodable", and generally refers to polymers or certain specific alloys, such as magnesium alloy, that are capable of being completely degraded and/or eroded when exposed to bodily fluids such as blood and can be gradually resorbed, absorbed, and/or eliminated by the body. The processes of breaking down and absorption of the polymer in a stent can be caused by, for example, hydrolysis and metabolic processes.

"A biodegradable stent" is used herein to mean a stent made from biodegradable polymers. Additional representative examples of polymers that may be used for making a biodegradable stent include, but are not limited to, poly(N-acetylglucosamine) (chitin), chitosan, poly(hydroxyvalerate), poly(lactide-coglycolide), poly(hydroxybutyrate), poly(hydloxybutyrateco-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrilestyrene copolymers, ABS resins, polyamides (such as Nylon 66 and polycaprolactam), polycarbonates, polyoxymethylenes, polyimides, polyethers, polyurethanes, rayon, rayontriacetate, cellulose, cellulose acetate, cellulose butyrate, cellulose acetate butyrate, cellophane, cellulose nitrate, cellulose propionate, cellulose ethers, and carboxymethyl cellulose. Another type of polymer based on poly(lactic acid) that can be used includes graft copolymers, and block copolymers, such as AB block-copolymers ("diblock-copolymers") or ABA block-copolymers ("triblock-copolymers"), or mixtures thereof.

Additional representative examples of polymers that may be suited for use in fabricating a biodegradable stent include ethylene vinyl alcohol copolymer (commonly known by the genetic name EVOI-I or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol. The properties and usages of these biodegradable polymers are known in the art, for example, as disclosed in U.S. Pat. No. 8,017,144 and U.S. application publication No. 2011/0,098,803.

In some aspects, a biodegradable stent as described herein may be made from polylactic acid (PLA), polyglycolic acid (PGA), poly(D,L-lactide-co-glycolide), polycaprolactone, or copolymers thereof.

In some aspects, a biodegradable stent as described herein may be made from polyhydroxy acids, polyalkanoates, polyanhydrides, polyphosphazenes, polyetheresters, polyesteramides, polyesters, and polyorthoesters.

In some preferable aspects, a biodegradable stent as described herein may be made from chitosan, collagen, elastin, gelatin, fibrin glue, or combinations thereof.

"Chitosan based stent", "chitosan stent" as described herein mean that the major component of a stent comes from chitosan. For example, a chitosan based stent as described herein may contain chitosan at least in an amount of over 50%, or over 60%, or over 70%, or over 80% weight percentage of the total stent weight. Even more particularly, a chitosan based stent as described herein may have the chitosan content in an amount of between about 70% and about 85% weight percentage of the total chitosan stent.

A chitosan based stent as described herein may also be coated with a polymer layer in order to adjust degradation times. For example, a chitosan based stent as described herein may be dip-coated with a solution of poly(D,L-lactide-co-glycolide) in acetone.

A chitosan based stent may also be coated with a layer of barium sulfate, by dipping the stents into an aqueous suspension of barium sulfate. In some aspects, the weight of the coated barium sulfate may be in an amount of between about 15 and between about 30 weight percentage of the total weight of the stent. Additionally, a chitosan stent may be perforated.

The stent designed according to the criteria of this disclosure may be a coronary stent, a vascular stent, or any other drug-containing implantable devices for vascular system as well any medical device that is effective in lowering the restenosis and thrombosis rates in a sustainable manner to secure patient safety in the long term.

In one embodiment, a thinner stent is used. However, the stent strut should have enough thickness which will ensure the stent structure stability, without the risk of breaking over time. As an example, the thickness of the stent for 316L stainless steel stent is about 100 to 110 um, and for the CoCr stent is about 80 um.

The Drug-Containing Layer:

The disclosure provides that there is a window of opportunity for vascular restoration of the endothelium after the implantation of a stent into a heart vessel in terms of patient safety and stent efficacy. In one embodiment, it is necessary for the re-endothelialization of the stent to be sufficiently accomplished and proper structural foundation of the endothelium or alignment of the endothelial cells is established within the window time period disclosed herein such that functional restoration of the endothelium coverage of the stent can be obtained and restenosis and/or thrombosis be significantly prevented or reduced. In one embodiment, sufficient re-endothelialization of the stent/vascular wall is obtained within the first 2-3 months such that the vascular endothelial function restoration can be achieved within 12 months. The sufficiency of the restoration of the endothelium can be determined by any means known in the industry. In animal models, this can be measured by methods that include Evans-blue staining (the presence of the staining is a negative marker for desirable endothelial cell layer functioning), VE-Cadherin/p120 staining (the presence of good overlap in staining is a positive marker of desirable endothelial cell layer functioning), and others. In vivo, it may for example be measured by neointimal coverage of the surface of stent struts, and neointimal thickness as measured by OCT methods known in art at different time points. For example, a thickness below a first threshold may be indicative that a sufficient foundation structure has not formed, which will result in less sufficient restoration of the function of the endothelial layer, while a thickness above a second, higher threshold may be indicative of a ratio of smooth muscle cells to endothelial cells that is too high, sometimes it is a good indication for over proliferation of the smooth muscle cells.

In one embodiment, endothelium restoration means that the right connection among the endothelial cells is re-established, and the biological function of the Endothelium is restored over the surface of the stent or along the vessel wall/neointima. Endothelium refers to a functional endothelial layer. Vascular functional restoration can be measured by any means known in the industry. For example, it can be measured by neointimal coverage of the surface of stent struts, and neointimal thickness as measured by OCT (e.g., one to three months) or other methods known in art at different time points (e.g., SEM examination of the stent coating). Other means that measure the function of the endothelium can also be used (Evan's blue (e.g., at 30, 60, and 90 days; should not stain the endothelial layer), VE cadherin/P120 confocal microscopy staining overlap is desirable).

In one embodiment, the drug eluting stent, is designed in such way that it can achieve complete drug release within 30 days, and substantial neointimal coverage at 3 months.

For the purposes of this disclosure, "complete drug release" from the stent (drug-containing layer) means release of from about 95% to about 100% of the drug, preferably from about 95%- to about 96%, from about 96%- to about 97%, from about 97%- to about 98%, from about 98% to about 99%, and from about 99%- to about 100% of the drug. Drug release is assessed in animal models (e.g., rabbit model) or in vitro models that are understood by one of ordinary skill in the art as predictable of drug release in the subject in which the stent of the disclosure is implanted. In one embodiment, "completely released" refers to a level at which the drug remaining is below detectable level and/or below a therapeutic level.

For the purposes of this disclosure, the drug-containing layer is said to have "completely dissolved" (also referred to as bio-degraded) when from about 95% to about 100% of the drug-containing layer, preferably from about 95%- to about 96%, from about 96%- to about 97%, from about 97%- to about 98%, from about 98% to about 99%, and from about 99%- to about 100% of the drug-containing layer has dissolved (also referred to as bio-degraded) from the stent.

Drug-containing layer dissolution (also referred to as bio-degradation) from the stent is assessed in animal models (e.g., rabbit model) or in vitro models that are understood by one of ordinary skill in the art as predictable of the drug-containing layer dissolution (also referred to as bio-degradation) from the stent in the subject in which the stent of the disclosure is implanted. In one embodiment, "completely dissolved" refers to a level at which the material remaining is below a detectable level.

A drug-containing layer (3) may be made from polymers and may comprise a layer or layers covering all or part of the stent surface. Furthermore, a drug-containing layer (3) may be capable of hosting a drug (4) and releasing the drug (4) in a sustained manner. Examples of the polymers using in drug-containing layer (3) may include, but are not limited to, poly(hydroxyalkanoates) (PHAs), poly(ester amides) (PEAs), poly(hydroxyalkanoate-co-ester amides), polyacrylates, polymethacrylates, polycaprolactones, poly(ethylene glycol)(PEG), poly(propylene glycol)(PPG), poly(propylene oxide) (PPO), poly(propylene fumarate) (PPF), poly(D-lactide), poly(L-lactide), poly(D,L-lactide), poly(meso-lactide), poly(L-lactide-co-meso-lactide), poly(D-lactide-co-meso-lactide), poly(D,L-lactide-co-meso-lactide), poly(D,L-lactide-co-PEG), poly(D,L-lactide-co-trimethylene carbonate), poly(lactide-co-glycolide), poly(glycolic acid-co-trimethylene carbonate), poly(trimethylene carbonate), PHA-PEG, PBT-PEG (PolyActive®), PEG-PPO-PEG (Pluronic®), and PPF-co-PEG, polycaprolactones, polyglycerol sebacate, polycarbonates, biopolyesters, polyethylene oxide, polybutylene terephalate, polydioxanones, hybrids, composites, collagen matrices with growth modulators, proteoglycans, glycosaminoglycans, vacuum formed small intestinal submucosa, fibers, chitin, dexran, and/or mixtures thereof.

The rate of degradation of the drug-containing polymer layer is generally determined by its composition. One of ordinary skill in the art may select one or more polymers using a standard PK animal test to confirm that the polymer(s) degrade between 45 and 60 days after implantation. In addition, a manufacturer of the polymer or the polymeric matrix may provide the degradation performance of the drug-containing polymer, e.g., the degradation curve. One of ordinary skill in the art may derive the rate of degradation of the drug-containing polymer(s) from the degradation performance and select the polymers) based on the rate of degradation.

In one embodiment, the drug-containing layer (3) may have a thickness between 1 and 200 µm, e.g., between 5 and 12 µm. In one embodiment, the drug-containing layer has a thickness between 3.5-10 µm. In one embodiment, the thickness of the abluminal side is between 1.5-200 µm and the thickness of the luminal side is between 1-66 µm.

In certain aspects, the drug-containing layer (3) may have an uneven coating thickness. For example, the coating thickness of the luminal side (6) and the lateral side (7) may be thinner than the abluminal side (8) of the stent. In one embodiment, a coating thickness ratio between the luminal side (6) and the abluminal side (8) may range from 2:3 to 1:7. Similarly, the coating thickness ratio between the lateral side (7) and the abluminal side (8) may range from 2:3 to 1:7. Accordingly, the drug release on the luminal side (6) and the lateral side (7) may be faster than the abluminal side (8). The faster release of the drug on the luminal side (6) and the lateral side (7) may enable faster restoration of endothelia layers on the luminal side (6) and the lateral side (7) compared with the abluminal side (8). In another embodiment, the coating thickness ratio between the luminal side (6) and the abluminal side (8) may be 1:1. Ranges provided herein are understood to be shorthand for all of the values within the range. For example, a range of 1 to 10 is understood to include any number, combination of numbers, or sub-ranges such as 1, 1.5, 2.0, 2.8, 3.90, 4, 5, 6, 7, 8, 9, and 10.

In some embodiments, the drug-containing layer (3) may be coated on the abluminal side (8) of the stent only. In such embodiments, the lack of drug release from the luminal side (6) and the lateral side (7) may enable the early restoration of endothelia layers on the luminal side (6) and the lateral side (7). In other embodiments, the drug release from the luminal side (6) and the lateral side (7) may be less than 15 days, or 10-20 days, which may enable the early restoration of endothelial layers on the luminal side (6) and the lateral side (7).

Moreover, in such embodiments, the degradation of polymer on the luminal side (6) and the lateral side (7) may be faster than the degradation of polymer on the abluminal side (8). For example, the polymer of the luminal side (6) and the lateral side (7) may comprise PLGA, and the polymer of the abluminal side (8) may comprise PLA. Generally, the degradation of PLGA is faster than PLA, and this information can be easily accessed from the polymer manufacturer.

In some embodiments, sometimes advantageously, a 30-day drug (4) release time frame and a 45-to-60-day drug-containing coating (3) bio-degradable/dissolution time frame may enable the functional restoration of endothelial layers. Within the time frame mentioned above, the restoration of the functional EC layer may be sufficiently completed in 90 days as measured in rabbit animal model. Then it may enable the long-term safety of the drug eluting stent in human. In one embodiment, the stent is unevenly coated by the drug containing layer, producing a thinner drug coating on the luminal or luminal side of the stent, which enables the drug to disappear from the stent between 10 to 20 days.

The drug-containing coating may soften, dissolve or erode from the stent to elute at least one bioactive agent. This elution mechanism may be referred to as surface erosion where the outside surface of the drug-polymer coating dissolves, degrades, or is absorbed by the body; or bulk erosion where the bulk of the drug-polymer coating biodegrades to release the bioactive agent. Eroded portions of the drug-polymer coating may be absorbed by the body, metabolized, or otherwise expelled.

The drug-containing coating may also include a polymeric matrix. For example, the polymeric matrix may include a caprolactone-based polymer or copolymer, or various cyclic polymers. The polymeric matrix may include various synthetic and non-synthetic or naturally occurring macromolecules and their derivatives. The polymer is advantageously selected in the group consisting of one or more biodegradable polymers in varying combinations, such as polymers, copolymers, and block polymers. Some examples of such biodegradable (also bio-resorbable or else bioabsorbable) polymers include polyglycolides, polylactides, polycaprolactones, polyglycerol sebacate, polycarbonates e.g. tyrosine derived, biopolyesters such as poly(β-hydroxyalcanoate)s (PHAs) and derived compounds, polyethylene oxide, polybutylene terephtalate, polydioxanones, hybrids, composites, collagen matrices with growth modulators, proteoglycans, glycosaminoglycans, vacuum formed SIS (small intestinal submucosa), fibers, chitin, and dextran. Any of these biodegradable polymers may be used alone or in combination with these or other biodegradable polymers in varying compositions. The polymeric matrix preferably includes biodegradable polymers such as polylactide (PLA), polyglycolic acid (PGA) polymer, poly (e-caprolactone) (PCL), polyacrylates, polymethacryates, or other copolymers. The pharmaceutical drug may be dispersed throughout the polymeric matrix. The pharmaceutical drug or the bioactive agent may diffuse out from the polymeric matrix to elute the bioactive agent. The pharmaceutical drug may diffuse out from the polymeric matrix and into the biomaterial surrounding the stent. The bioactive agent may separate from within the drug-polymer and diffuse out from the polymeric matrix into the surrounding biomaterial. In a further embodiment the drug coating composition may be fashioned using the drug 42-Epi-(tetrazolyl)-Sirolimus, set forth in U.S. Pat. No. 6,329,386 assigned to Abbott Laboratories, Abbott Park, Ill. and dispersed within a coating fashioned from phosphorylcholine coating of Biocompatibles International P.L.C. set forth in U.S. Pat. No. 5,648,442.

The polymeric matrix of the drug-containing layer may be selected to provide a desired elution rate of the drug/bioactive agent. The pharmaceutical drugs may be synthesized such that a particular bioactive agent may have two different elution rates. A bioactive agent with two different elution rates, for example, would allow rapid delivery of the pharmacologically active drug within twenty-four hours of surgery, with a slower, steady delivery of the drug, for example, over the next two to six months. The electrografted primer coating may be selected to firmly secure the polymeric matrix to the stent framework, the polymeric matrix containing the rapidly deployed bioactive agents and the slowly eluting pharmaceutical drugs.

In some embodiments, a drug (4) may be encapsulated in the drug-containing layer (3) using a microbead, microparticle or nanoencapsulation technology with albumin, liposome, ferritin or other biodegradable proteins and phospholipids, prior to application on the primer-coated stent.

The Drug or Bioactive Agent

By way of example, drug (4) may include, for example, antithrombogenic agent, an anticoagulant, an antiplatelet agent, an antineoplastic agent, an antiproliferative agent, an antibiotic, an anti-inflammatory agent, a gene therapy agent, a recombinant DNA product, a recombinant RNA product, a collagen, a collagen derivative, a protein analog, a saccharide, a saccharide derivative, an inhibitor of smooth muscle cell proliferation, a promoter of endothelial cell migration, proliferation, and/or survival, and combinations of the same. In one embodiment, the drug is an anti-angiogenic drug. In another embodiment, the drug is an angiogenic drug. In some embodiments, the drug/bioactive agent may control cellular proliferation. The control of cell proliferation may include enhancing or inhibiting the growth of targeted cells or cell types. In some embodiments, the cells are vascular smooth muscle cells, endothelial cells, or both. In some embodiments, the drug suppresses the proliferation of smooth muscle cells and/or promotes the proliferation of endothelial cells.

More broadly, drug (4) may be any therapeutic substance that provides a therapeutic characteristic for the prevention and treatment of disease or disorders. For example, an antineoplastic agent may prevent, kill, or block the growth and spread of cancer cells in the vicinity of the stent. In another example, an antiproliferative agent may prevent or stop cells from growing. In yet a further example, an antisense agent may work at the genetic level to interrupt the process by which disease-causing proteins are produced. In a fourth example, an antiplatelet agent may act on blood platelets, inhibiting their function in blood coagulation. In a fifth example, an antithrombogenic agent may actively retard blood clot formation. According to a sixth example, an anticoagulant may delay or prevent blood coagulation with anticoagulant therapy, using compounds such as heparin and coumarins. In a seventh example, an antibiotic may kill or inhibit the growth of microorganisms and may be used to combat disease and infection. In an eighth example, an anti-inflammatory agent may be used to counteract or reduce inflammation in the vicinity of the stent. According to a ninth example, gene therapy agent may be capable of changing the expression of a person's genes to treat, cure or ultimately prevent disease. In addition, an organic drug may be any small-molecule therapeutic material, and, similarly, a pharmaceutical compound may be any compound that provides a therapeutic effect. A recombinant DNA product or a recombinant RNA product may include altered DNA or RNA genetic material. In another example, bioactive agents of pharmaceutical value may also include collagen and other proteins, saccharides, and their derivatives. For example, the bioactive agent may be selected to inhibit vascular restenosis, a condition corresponding to a narrowing or constriction of the diameter of the bodily lumen where the stent is placed.

Alternatively or concurrently, the bioactive agent may be an agent against one or more conditions, including, but not limited to, coronary restenosis, cardiovascular restenosis, angiographic restenosis, arteriosclerosis, hyperplasia, and other diseases and conditions. For example, the bioactive agent may be selected to inhibit or prevent vascular restenosis, a condition corresponding to a narrowing or constriction of the diameter of the bodily lumen where the stent is placed. The bioactive agent may alternatively or concurrently control cellular proliferation. The control of cell proliferation may include enhancing or inhibiting the growth of targeted cells or cell types.

Examples of antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax™ (bivalirudin, Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide, nitric oxide donors, super oxide dismutases, super oxide dismutase mimetic, 4-amino-2,2,6,6-tetramethylpiperidine-1-oxyl (4-amino-TEMPO), estradiol, dietary supplements such as various vitamins, and combinations thereof.

In some embodiments, the bioactive agent may include podophyllotoxin, etoposide, camptothecin, a camptothecin analog, mitoxantrone, Sirolimus (rapamycin), everolimus, zotarolimus, Biolimus A9, myolimus, deforolimus, AP23572, tacrolimus, temsirolitnus, pimecrolimus, novolimus, zotarolimus (ABT-578), 40-O-(2-hydroxy)ethyl-rapamycin everolimus), 40-O-(3-hydroxypropyl)rapamycin, 40-O-[2-(2-hydroxy)ethoxy]ethyl-rapamycin, 40-O-tetrazolylrapamycin, 40-epi-(N1-tetrazolyl)-rapamycin, and their derivatives or analogs. Podophyllotoxin is generally an organic, highly toxic drug that has antitumor properties and may inhibit DNA synthesis. Etoposide is generally an antineoplastic that may be derived from a semi-synthetic form of podophyllotoxin to treat monocystic leukemia, lymphoma, small-cell lung cancer, and testicular cancer. Camptothecin is generally an anticancer drug that may function as a topoisomerase inhibitor. Related in structure to camptothecin, a camptothecin analog, such as aminocamptothecin, may also be used as an anticancer drug. Mitoxantrone is an anticancer drug generally used to treat leukemia, lymphoma, and breast cancer. Sirolimus is a medication that generally interferes with the normal cell growth cycle and may be used to reduce restenosis. The bioactive agent may alternatively or concurrently include analogs and derivatives of these agents. Antioxidants may be used in combination with or individually from the examples above for their antirestonetic properties and therapeutic effects.

The anti-inflammatory agent can be a steroidal anti-inflammatory agent, a nonsteroidal anti-inflammatory agent, or a combination thereof. In some embodiments, anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, henzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof.

For the removal of blood clots and thrombus, examples of therapeutic agents may include (i) tissue plasminogen activator, tPA, BB-10153, rTPA, Urokinase, Streptokinase, Alteplase and Desmoteplase, (ii) antiplatelet agents such as aspirin. Clopidorgel and Ticclopidine, and (iii) GIIb/IIIa inhibitors, such as Abciximab, Tirofiban and Eptifibatide.

The dosage or concentration of the drug required to produce a favorable therapeutic effect should be less than the level at which the drug produces toxic effects and greater than the level at which non-therapeutic results are obtained. This applies to an antiproliferative agent, a prohealing agent, or any other active agent included in any of the various embodiments of the invention. Therapeutically effective dosages can also be determined from an appropriate clinical study, such as but not limited to, a Phase II or Phase III study. Effective dosages can also be determined by the application of an appropriate pharmacokinetic-pharmacodynamic model in human, or other animals. Standard pharmacological test procedures to determine dosages are understood by one of ordinary skill in the art. In some embodiments, the stent has a drug content of from about 5 µg to about 500 µg. In some embodiments, the stent has a drug content of from about 100 µg to about 160 µg. In one embodiment, the content of the drug in the drug-containing layer is from 0.5-50% by weight. In other embodiments, the drug-containing layer comprises from 0.5-10 µg/mm2 of drug (e.g., 1.4 µg/mm2).

When the drug eluting stent (1) is implanted into the human body vessel, the drug (4) may be released from drug-containing coating (3) within 30 days. Alternatively, for example, the drug may be released within 45 days, 60 days, or 120 days. The rate of drug release may be measured through a standard PK animal study, in which the fluid samples and tissues and the stents are extracted from animals at selected time points, and the concentration of drugs measured to best design the properties of the stent. These animal studies are reasonably predictive of what happens in humans, as well understood by one of ordinary skill in the art. Moreover, in embodiments where the drug-containing coating (3) is made from a bio-degradable or bio-absorbable polymer, the polymer may be bio-degraded or bio-absorbed between 45 days and 60 days. For example, 50:50 PLGA (as described in Example 1 below) may exhibit in vivo degradation time of about 60 days.

The Biocompatible Base Layer (5)

Over the stent framework (2), and underneath the drug-containing layer (3), a biocompatible base layer (5) may be formed, which may have a better biocompatible surface than the stent framework (2). For example, compared with a bare metal surface of the framework, the biocompatible surface of biocompatible base layer (5) may enable the early functional restoration of endothelia layers on a luminal side (6) and a lateral side (7) of the stent, which may result in a faster rate of migration and replication of the EC compared with a bare metal surface.

The biocompatible base layer (5) may be made from poly n-butyl methacrylate, PTFE, PVDF-HFP, poly(styrene-b-isobutylene-b-styrene), Parylene C, PVP, PEVA, SBS, PC, TiO2 or any material has good biocompatibility (or combinations thereof). In one embodiment, the base layer comprises or consists essentially of PBMA.

Other Materials

All embodiments may also include additional components such as, but not limited to, lubricating agents, fillers, plasticizing agents, surfactants, diluents, mold release agents, agents which act as active agent carriers or binders, anti-tack agents, anti-foaming agents, viscosity modifiers, potentially residual levels of solvents, and potentially any other agent which aids in, or is desirable in, the processing of the material, and/or is useful, or desirable, as a component of the final product, or if included in the final product.

Methods of Using the Stents:

In one embodiment, a stent is a medical device used for improving a stenosed region or an occluded region in a lumen in an organism such as a blood vessel, a bile duct (often, plastic stents) a trachea, an esophagus, an airway, an urethra or the like. Stents are inserted into these and other hollow organs to ensure that these hollow organs maintain sufficient clearance.

One use for medical stents is to expand a body lumen, such as a blood vessel, which has contracted in diameter through, for example, the effects of lesions called atheroma or the occurrence of cancerous tumors. Atheroma refers to lesions within arteries that include plaque accumulations that can obstruct blood flow through the vessel. Over time, the plaque can increase in size and thickness and can eventually lead to clinically significant narrowing of the artery, or even complete occlusion. When expanded against the body lumen, which has contracted in diameter, the medical stents provide a tube-like support structure inside the body lumen. Stents also can be used for the endovascular repair of aneurysms, an abnormal widening or ballooning of a portion of a body lumen which can be related to weakness in the wall of the body lumen.

Stents are used not only for mechanical intervention but also as vehicles for providing biological therapy, Biological therapy uses medicated stents to locally administer a therapeutic substance. The therapeutic substance can also mitigate an adverse biological response to the presence of the stent. A medicated stent (i.e., a stent comprising a drug) may be fabricated by the methods disclosed herein to include a polymeric carrier that includes an active or bioactive agent or drug.

In one embodiment, the stent is used in methods of treating a disease or disorder in a subject. Examples of disease or disorders where the stent can be used include diseases of the vasculature (heart disease, thrombosis), tumors, angioma, obstruction of lacrimal gland and other diseases of a lumen. The stent can be used for percutaneous coronary intervention (PCI) as well as in peripheral applications, such as the superficial femoral artery (SFA). In some embodiments, the stent can be used for the treatment of angiostenosis or to prevent restenosis, by utilizing a cell proliferation-suppressing agent such as cytostatic (e.g., paclitaxel) or immunosuppressant as the drug. In some embodiments, a ureteral stent of the disclosure is introduced into the kidney and/or the bladder of a subject.

As used herein, the term "subject" refers to human and non-human animals, including veterinary subjects. The term "non-human animal" includes all vertebrates, e.g., mammals and non-mammals, such as non-human primates, mice, rabbits, sheep, dog, cat, horse, cow, chickens, amphibians, and reptiles. In a preferred embodiment, the subject is a human and may be referred to as a patient.

As used herein, the terms "treat," "treating" or "treatment" refers, preferably, to an action to obtain a beneficial or desired clinical result including, but not limited to, alleviation or amelioration of one or more signs or symptoms of a disease or condition, diminishing the extent of disease, stability (i.e., not worsening) state of disease, amelioration or palliation of the disease state, diminishing rate of or time to progression, and remission (whether partial or total), whether detectable or undetectable. "Treatment" can also mean prolonging survival as compared to expected survival in the absence of treatment. Treatment does not need to be curative.

Methods of Introducing the Stent into the Subject

In one embodiment, the stent is introduced into the subject body via a catheter, or by implantation. In other embodiments, the stent is introduced by balloon catheter.

The terms "inserting a stent", "delivering a stent", "placing a stent", "employing a stent", and similar expressions as described herein all mean introducing and transporting a stent through a bodily lumen into a region that requires treatment by a mechanism such as a guidewire, balloon catheter, or other delivery system for self-expanding stents. In general, it is done by positioning a stent on one end of the guidewire, inserting the end of the guidewire through the bodily lumen of a subject, advancing the guidewire in the bodily lumen to a treatment site, and removing the guidewire from the lumen. The insertion may also be facilitated by other accessories such as a delivery sheath, a push rod, a catheter, a pusher, a guide catheter, an endoscope, a cystoscope, or a fluoroscopy. Other methods of delivering a stent are well known in the art.

The Manufacturing Process

Take Metal Stent Frame for Example:

1) Stent Manufacture

The stent frame can be laser cut from a metal tubing. After the laser cutting, the stent frame will undergo an electro-polishing process to make the edge of the stent frame smooth.

2) Base Layer Manufacture

Place the stent frame into a reservoir full of butylmethacrylate (monomer). During the electro-grafting process, the polymerization of butylmethacrylate will be initiated by some initiators and the base layer (Poly-butylmethacrylate) will be bonded (covalent bond) on the stent frame to provide surface with a better biocompatibility.

3) Drug Containing Layer Manufacture

50/50 PLGA (biodegradable polymer) and Sirolimus (drug) is mixed with a certain weight ratio and dissolved in chloroform to make the spray solution. The stent frame with base layer is fixed onto a rotator and spray coated with the spray solution.

Examples of Making the Stent Framework (2):

In some embodiments, the stent framework may comprise a pre-fabricated mesh of magnesium alloy. The alloy may be fully biodegradable between six and nine months after implantation. Additionally or alternatively, the stent framework may maintain mechanical radical strength for at least three months. Similarly, the stent framework may comprise a pre-fabricated Poly-L-lactic acid (PLLA) or other biocompatible fully biodegradable polymers. Such polymers may maintain the mechanical radical strength for at least three months.

In some embodiments, the stent framework may be cut from a metal tubing, e.g., using a laser. An electro-polishing process may smooth the stent framework after cutting.

Examples of Making the Biocompatible Base Layer (5):

Electrochemical Reaction

In one embodiment, n-butyl methacrylate monomer may be dissolved into N,N dimethyl formamide solvent (DMF). In certain aspects, sodium chloride may be added as an electrolyte to increase the conductivity of the solution. The solution may be rotated and mixed for 120 minutes. In one example, the concentration of methacrylate may be 20%, the concentration of sodium chloride may be $5.0 \times 10^{-2}$M, and the concentration of DMF may be 80%.

A reactor containing the above primer layer coating solution may use an electrochemical reaction to coat the stent framework with the solution. For example, the reactor may use a voltage of 20V to coat the framework at a pressure of 2 bar for approximately 120 minutes. The reactor may include a nitrogen environment.

The biocompatible base layer may then be baked in vacuum (e.g., at 10 mbar or less). In one example, the baking may occur at approximately 40° C. for 180 minutes. A biocompatible base layer formed with this process may have a thickness of approximately 200 nm.

Examples of Making the Drug-Containing Layer (3):

In one embodiment, the drug-containing layer is applied to the stent via a spray coating process. In other embodiments, the process of application of the drug-containing layer to the stent (directly or on the surface of the biocompatible base layer) comprises, for example, dipping, vapor deposition, and/or brushing.

Example 1

Spray Coating Process

A. Process

In some embodiments, the drug-containing layer (3) may be formed using a spray coating process for disposing a polymer coating on the stent framework (or on a polymer-coated stent, e.g., a stent coated in the electro-grated coating described below). In one example, a 20 millimeter long electro-grafted stent was spray coated with biodegradable polyester (polylactide-co-glycolide 50/50, PLGA) containing Sirolimus. The copolymer (0.25% w/v) was dissolved in chloroform. Sirolimus was then dissolved in the chloroform/polymer mixture to obtain a final ratio Sirolimus/polymer of (1/5). In another example, the mixture may comprise 50/50 PLGA (e.g., 5 g) with rapamycin 0.5 g) dissolved in chloroform (e.g., 600 mL). The mixture was then applied to the stent, mounted on rotative mandrel, by spraying with a fine nozzle with the following parameters:

| Spray parameter | |
|---|---|
| Spraying flow (µL/s) | 24 |
| Spraying volume (µL/s) | 192 |
| Pressure (bar) | 0.3 |
| Stent rotation speed (rpm) | 2000 |
| Nozzle/stent distance (mm) | 6.5 |
| Number of spray run | 50 |

Alternatively, such parameters may be adjusted by one of ordinary skill in the art to meet the conditions of this disclosure, to produce a un-even distribution of the drug layer on the stent surface (thinner on the luminal face). In some embodiments, the parameters can be adjusted from those used in U.S. patent application Ser. No. 13/850,679 (published as 2014/0296967 A1), U.S. patent application Ser. No. 11/808,926 (published as 2007/0288088 A1), and U.S. Provisional Patent Application No. 60/812,990, all of which are incorporated herein by reference in their entireties.

Figure 10:
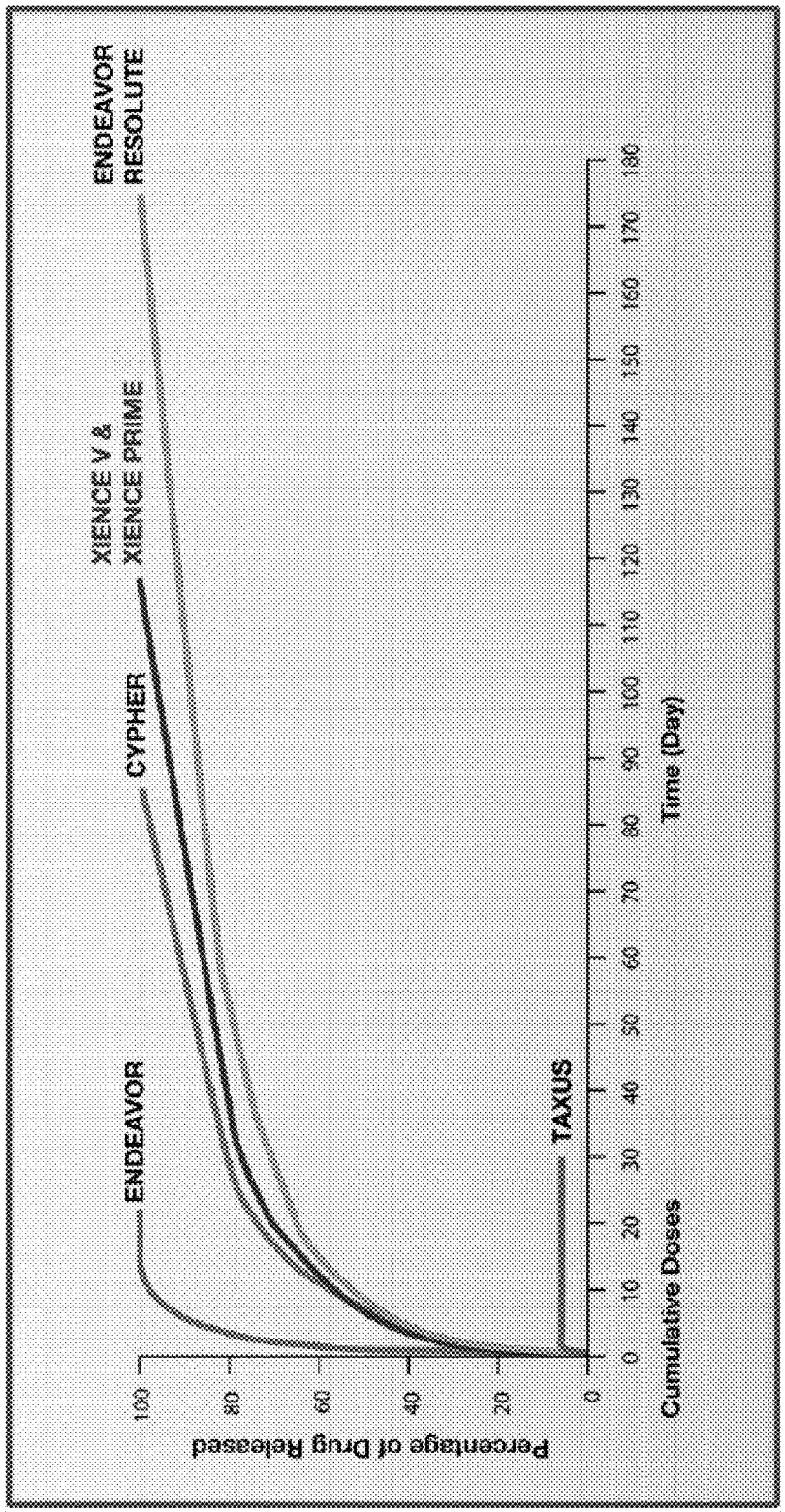
FIG. 10 shows the drug release time frame of a XIENCE V stent and a XIENCE PRIME as about 120 days. The drug release time of ENDEAVOR RESOLUTE (i.e., a stent according to some embodiments of the present disclosure) as about 180 days.
Figure 11:
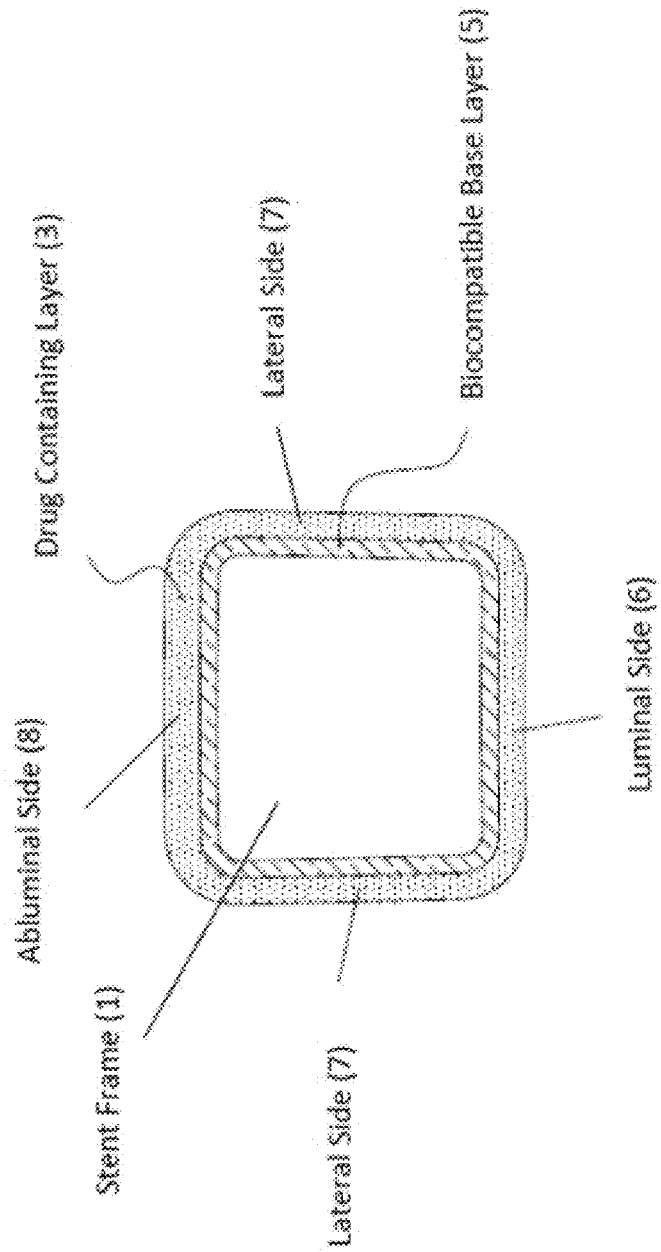
FIG. 11 shows the relative position of layers of a stent according to some embodiments of the present disclosure. The luminal side (6) faces the blood flow, and the abluminal side (8) faces or contacts the vessel wall.
Figure 12A:
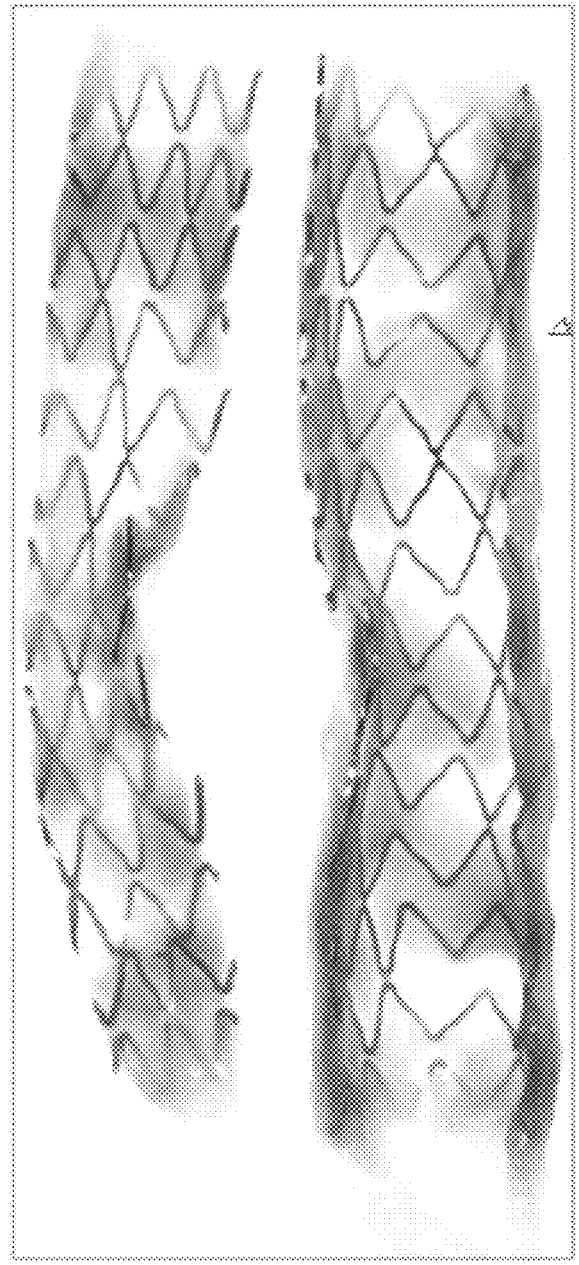
FIG. 12A depicts a drug eluting stent, according to some embodiments of the present disclosure, 45 days after implantation imaged using Evans Blue uptake, in which the positive stained area was 28.57%.
Figure 12B:
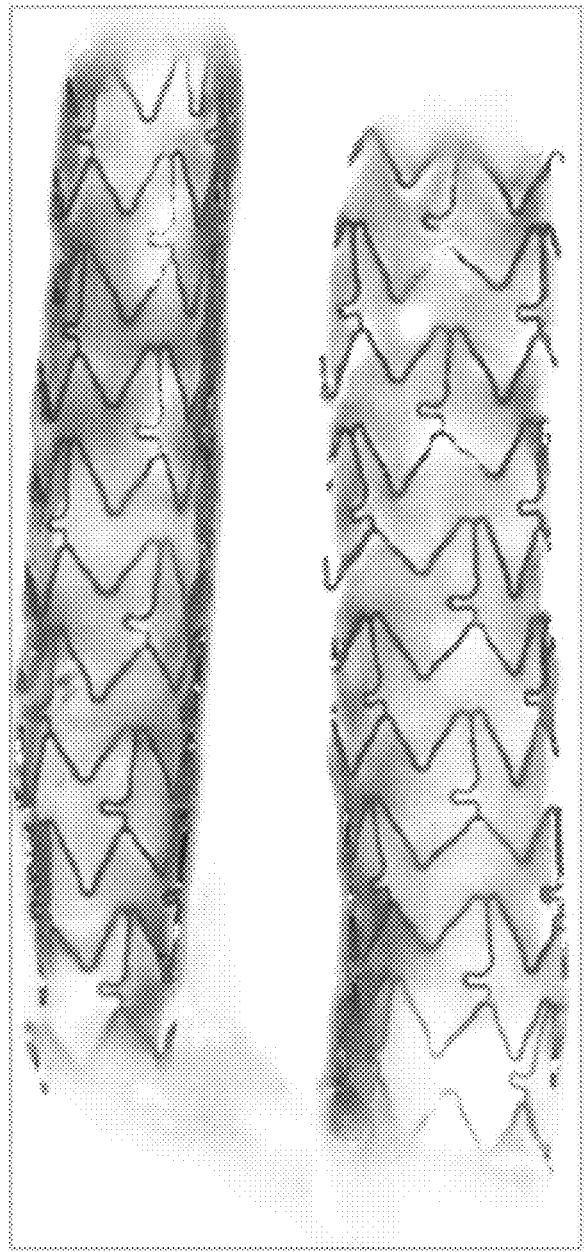
FIG. 12B depicts a drug eluting stent 45 days after implantation using Evans Blue uptake, in which the positive stained area was 55.0%.
Figure 12C:
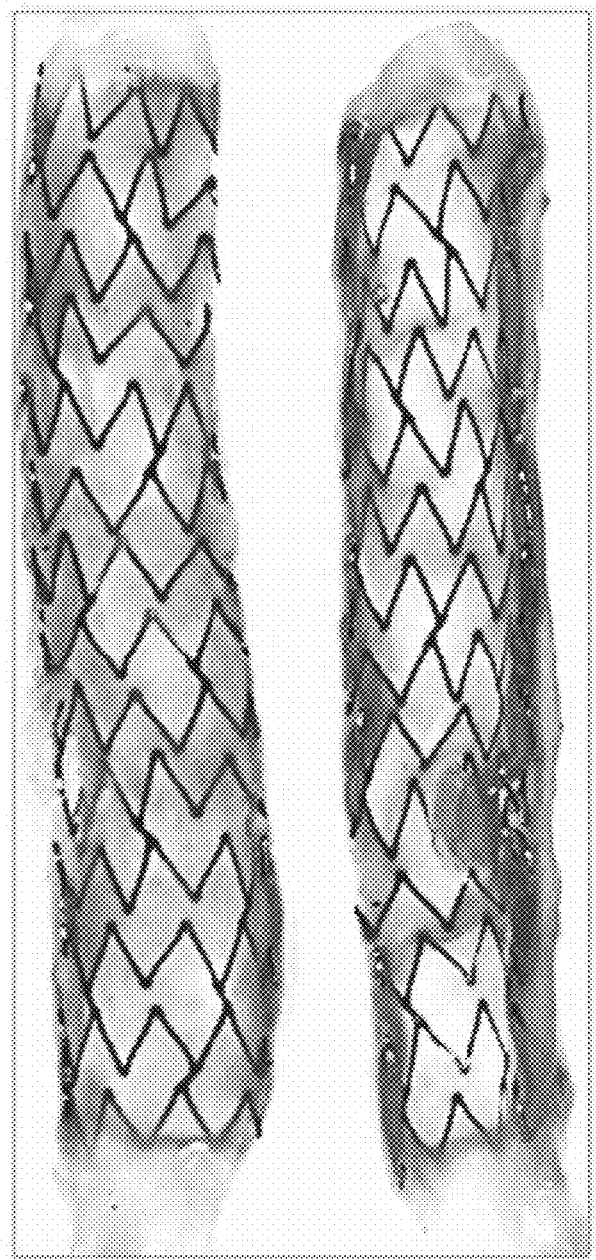
FIG. 12C depicts a drug eluting stent 45 days after implantation imaged using Evans Blue uptake, in which the positive stained area was 56.79%.
Figure 13A:
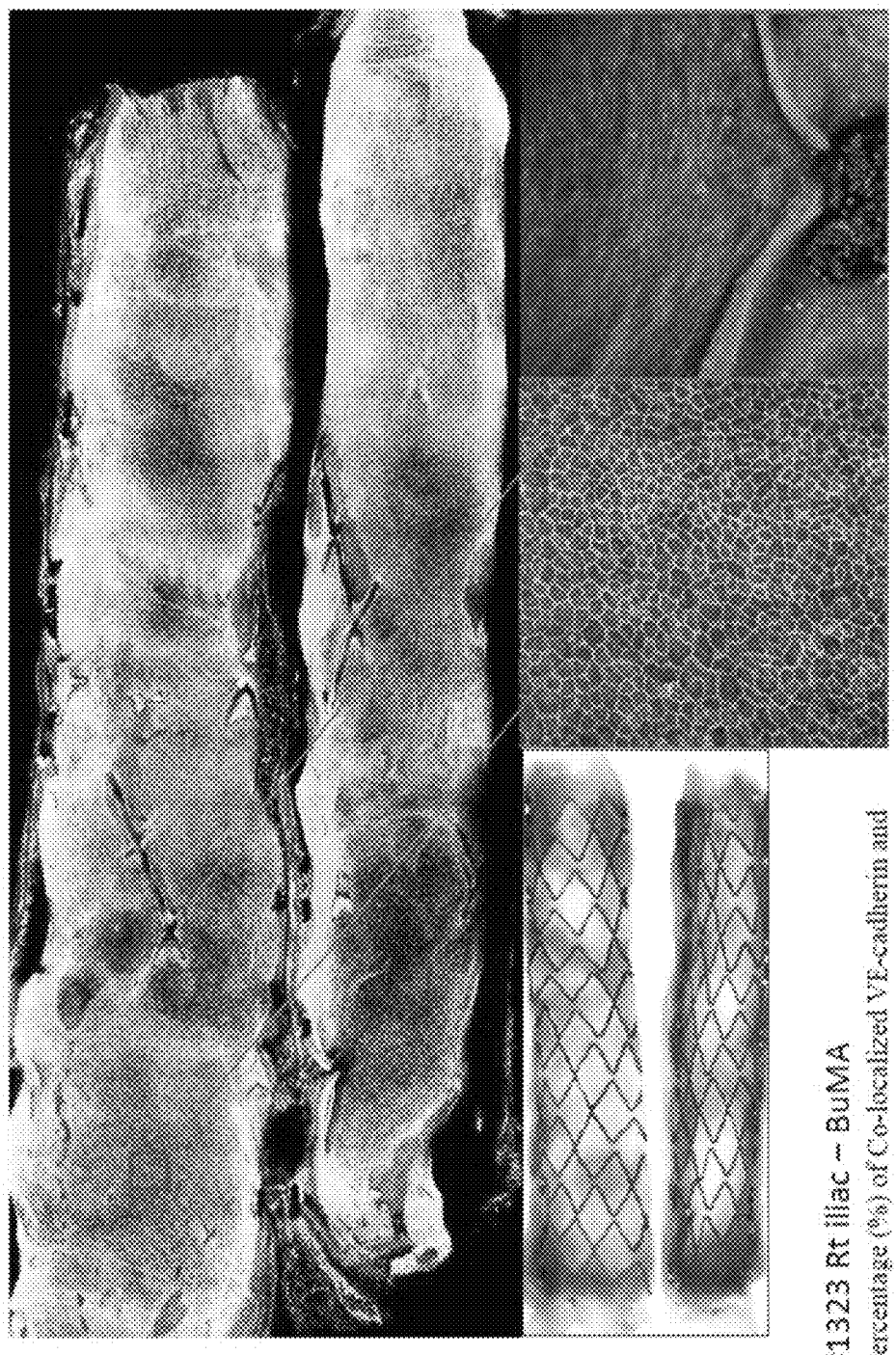
FIG. 13A depicts a drug eluting stent, according to some embodiments of the present disclosure, 45 days after implantation showing a confocal microscope image of a region of the drug eluting stent with 20× objective, where the region had evidence of competent endothelial barrier function (that is, co-localized p120/VE-cadherin). VE Cadherin was red channel (555 nm), P120 was green channel (488 nm), and blue channel (405 nm) was DAPI counterstain.
Figure 13B:
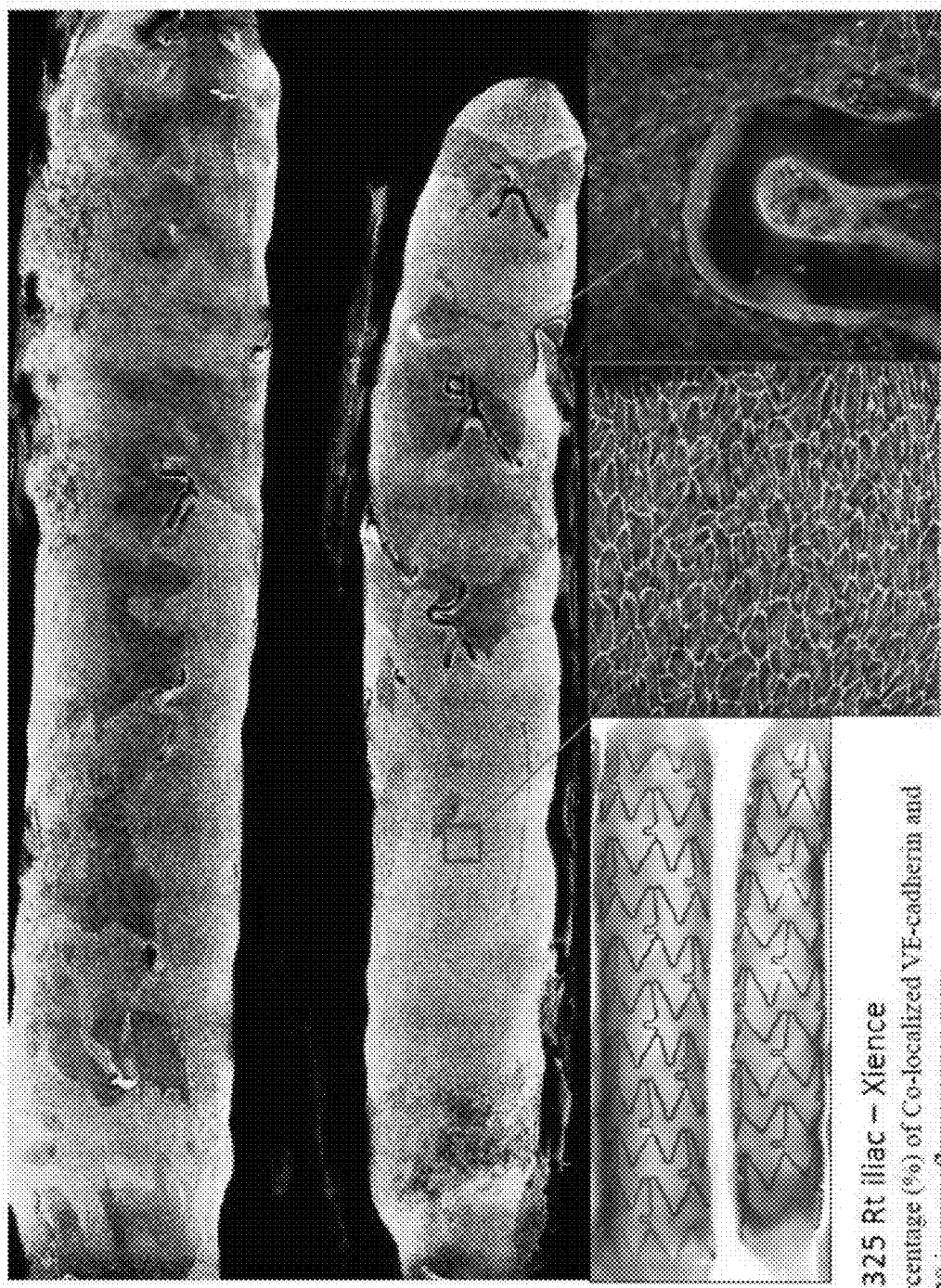
FIG. 13B depicts a drug eluting stent 45 days after implantation showing a confocal microscope image of a region of the drug eluting stent with 20× objective, where the region had evidence of competent endothelial barrier function (that is, co-localized p120/VE-cadherin). VE Cadherin was red channel (555 nm), P120 was green channel (488 nm), and blue channel (405 nm) was DAPI counterstain.
Figure 13C:
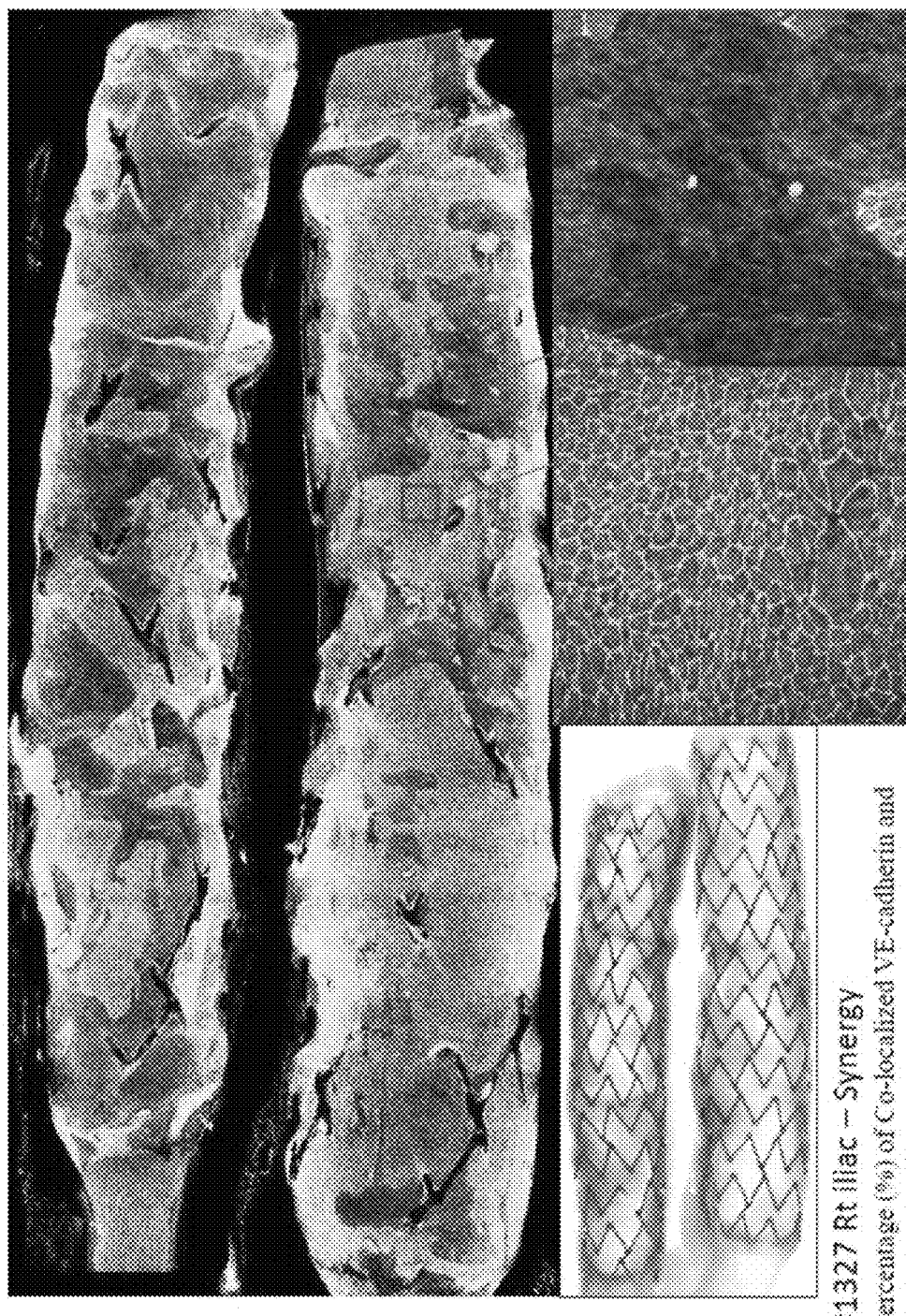
FIG. 13C depicts a drug eluting stent 45 days after implantation showing a confocal microscope image of a region of the drug eluting stent with 20× objective, where the region had evidence of competent endothelial barrier function (that is, co-localized p120/VE-cadherin). VE Cadherin was red channel (555 nm), P120 was green channel (488 nm), and blue channel (405 nm) was DAPI counterstain.
Figure 14A:
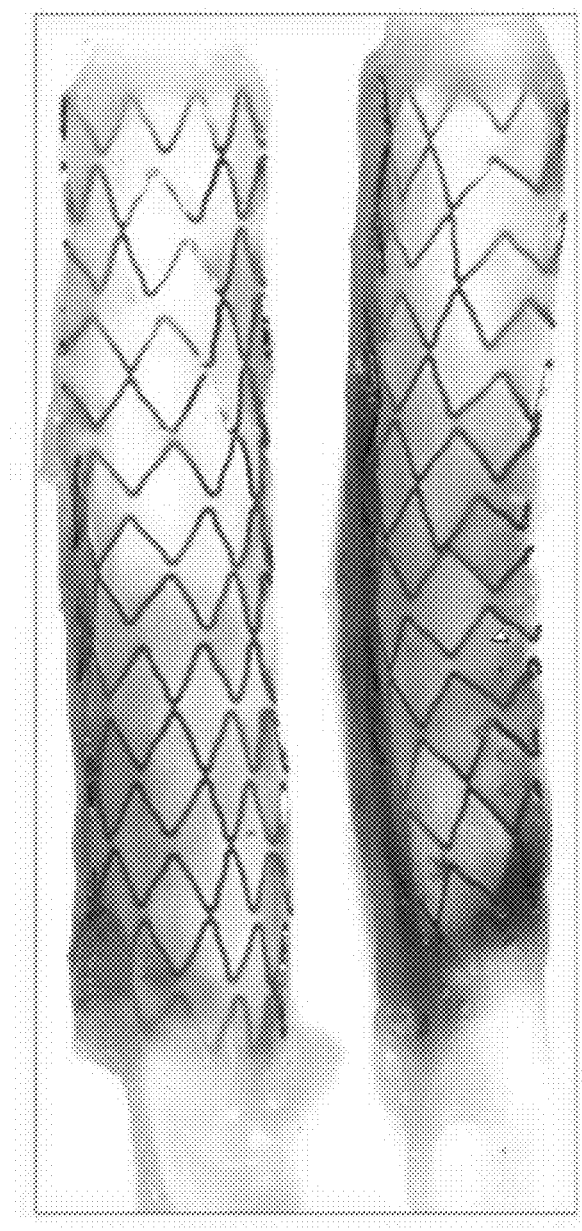
FIG. 14A depicts a drug eluting stent, according to some embodiments of the present disclosure, 90 days after implantation imaged using Evans Blue uptake, in which the positive stained area was 23.21%.
Figure 14B:
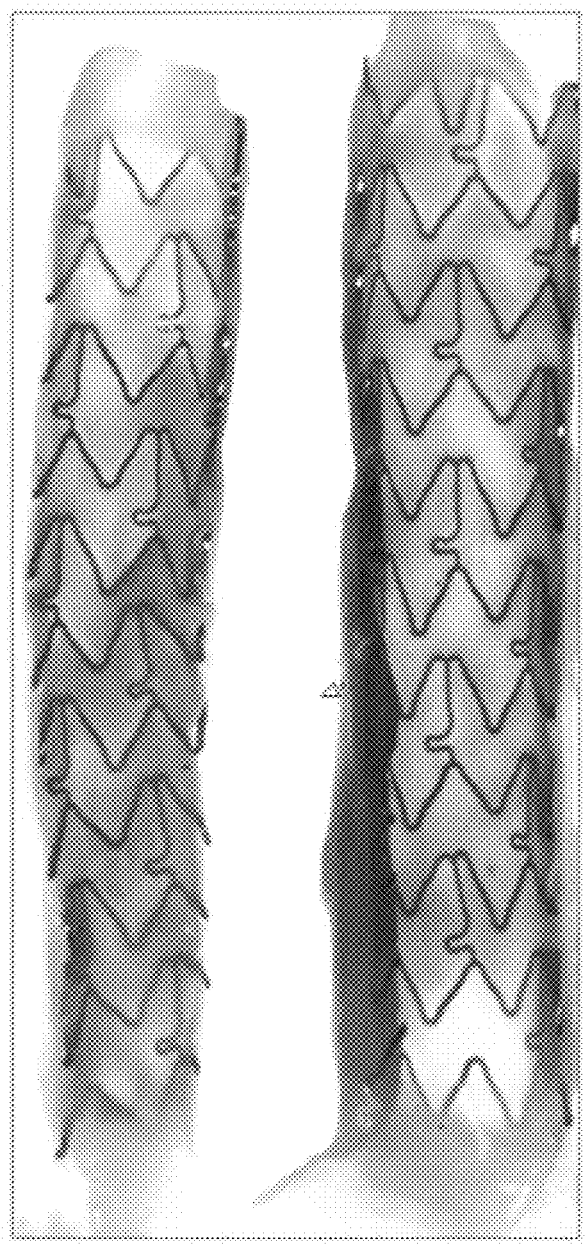
FIG. 14B depicts a drug eluting stent 90 days after implantation using Evans Blue uptake, in which the positive stained area was 42.95%.
Figure 14C:
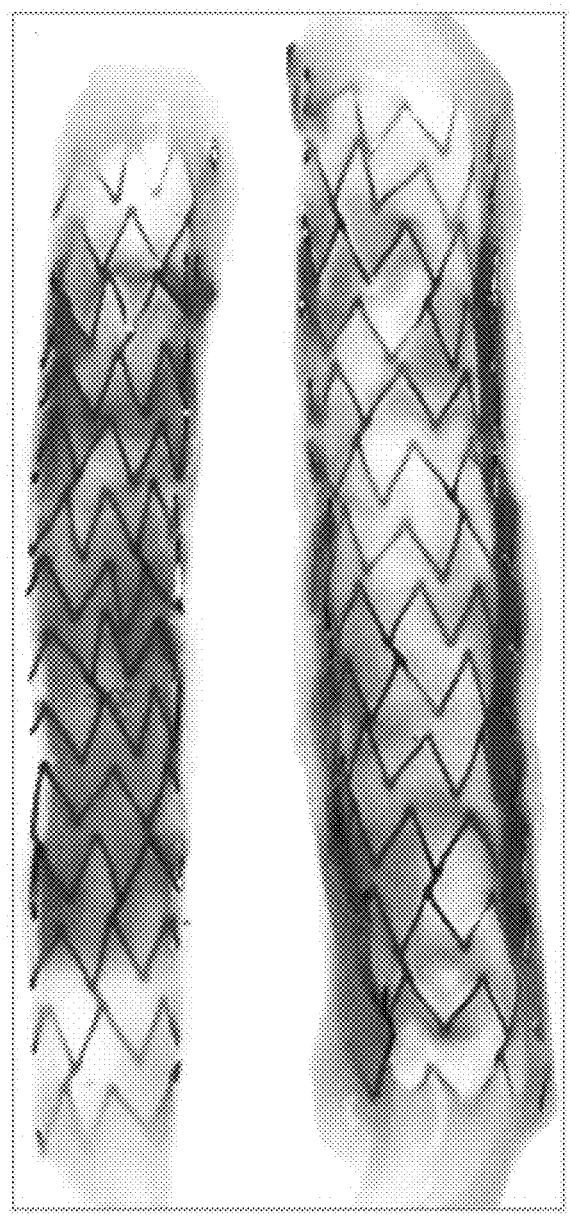
FIG. 14C depicts a drug eluting stent 90 days after implantation imaged using Evans Blue uptake, in which the positive stained area was 41.79%.
Figure 15A:
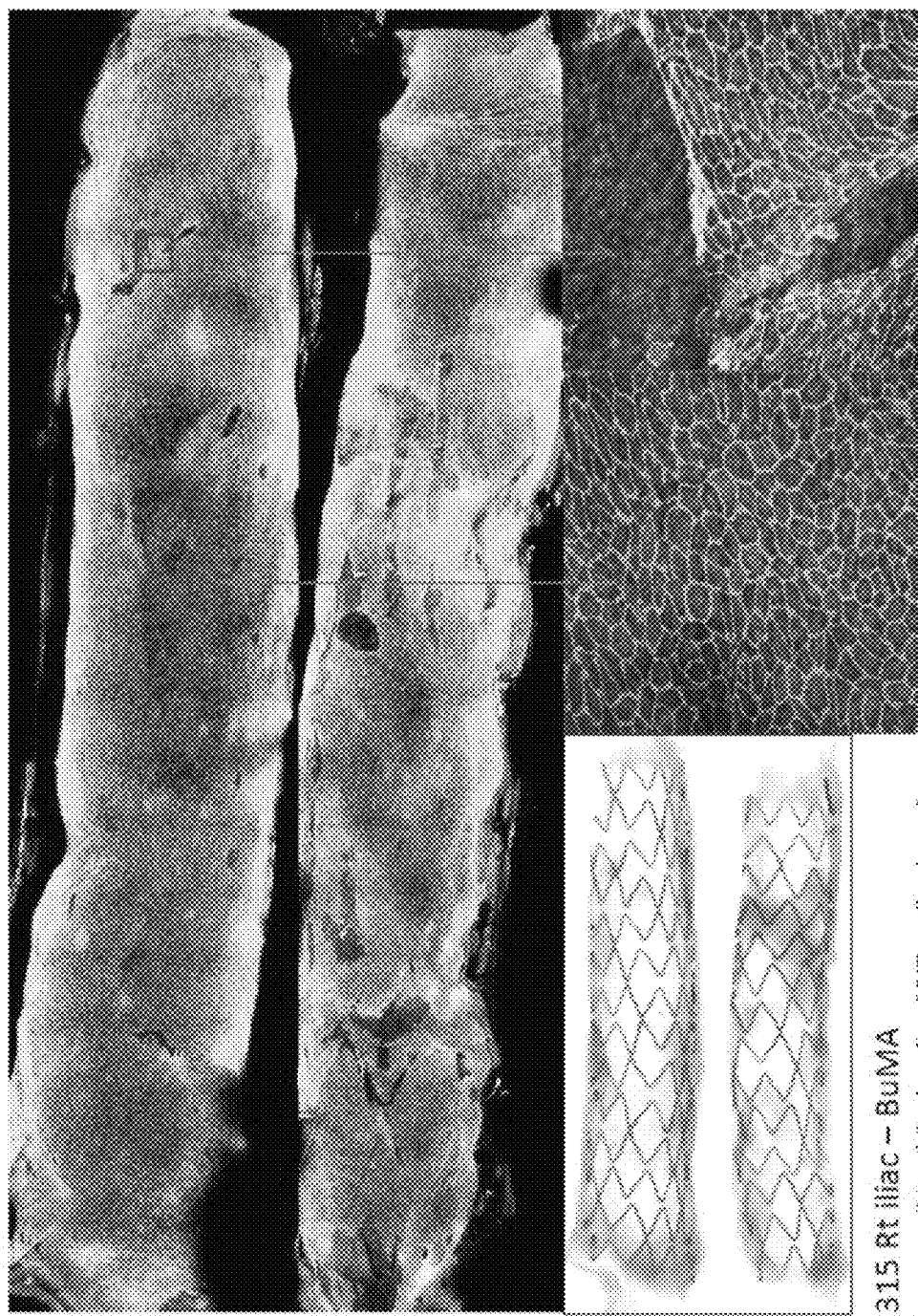
FIG. 15A depicts a drug eluting stent, according to some embodiments of the present disclosure, 90 days after implantation showing a confocal microscope image of a region of the drug eluting stent with 20× objective, where the region had evidence of competent endothelial barrier function (that is, co-localized p120/VE-cadherin). VE Cadherin was red channel (555 nm), P120 was green channel (488 nm), and blue channel (405 nm) was DAPI counterstain.
Figure 15B:
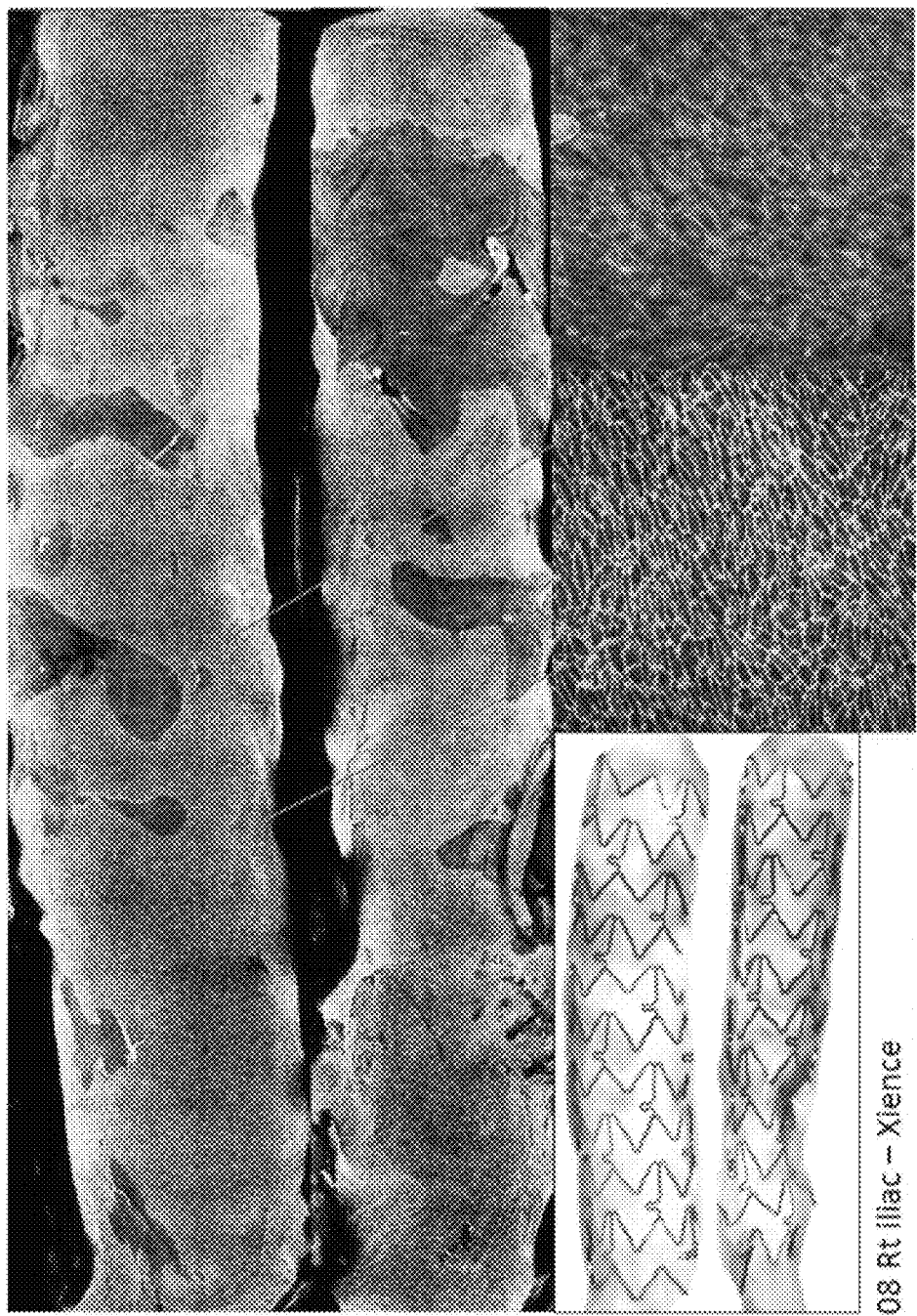
FIG. 15B depicts a drug eluting stent 90 days after implantation showing a confocal microscope image of a region of the drug eluting stent with 20× objective, where the region had evidence of competent endothelial barrier function (that is, co-localized p120/VE-cadherin). VE Cadherin was red channel (555 nm), P120 was green channel (488 nm), and blue channel (405 nm) was DAPI counterstain.
Figure 15C:
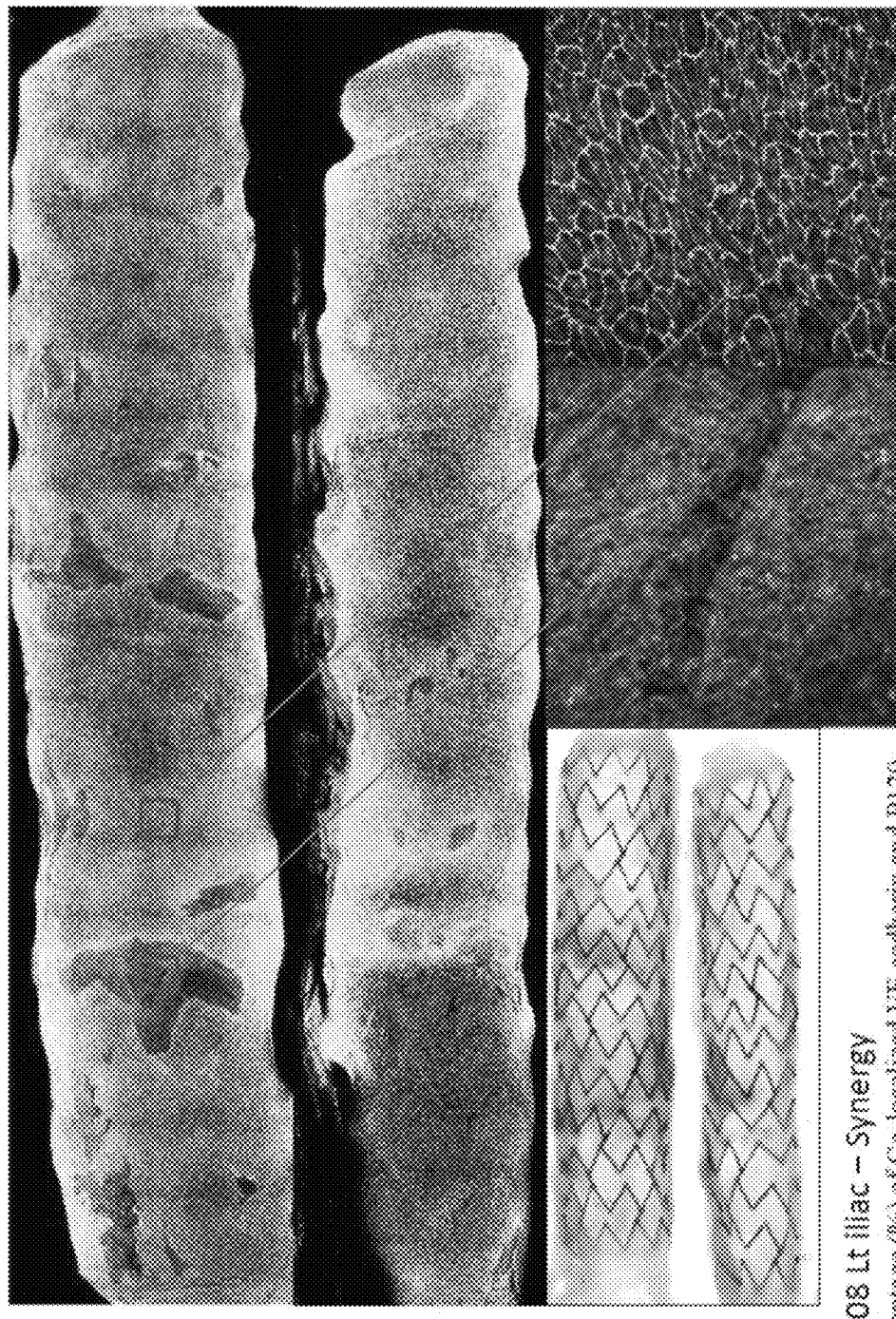
FIG. 15C depicts a drug eluting stent 90 days after implantation showing a confocal microscope image of a region of the drug eluting stent with 20× objective, where the region had evidence of competent endothelial barrier function (that is, co-localized p120/VE-cadherin). VE Cadherin was red channel (555 nm), P120 was green channel (488 nm), and blue channel (405 nm) was DAPI counterstain.

The conditions of the drug spraying may be adjusted so that the drug-containing coating (3) may be applied to a luminal side (6), lateral side (7), and abluminal side (8) of the stent. See FIG. 10. Due to the high speed rotation spray and centrifugal effect, drug-containing coating (3) may have a higher (and tunable) thickness on the abluminal side (facing the vessel wall) (8) with respect to the luminal side (facing the blood flow) (6) and the lateral side (7). An embodiment of this disclosure is a stent with such an un-even coating. In one embodiment, relative high speed spinning, and low pressuring process over coating the stent with the drug-containing solution was found to produce this result. Drying at 40° C. was then performed in a vacuum oven. Using the above parameters, the coating on this example stent weighs 800+/−80 μg and has a thickness of about 5-7 μm. The drug loading in this example stent was 164+/−16 μg.

B. In Vivo Studies in Rabbits

Stents prepared by this method were used in vivo. A first stent was prepared according to this example method with the following stent framework structure: In this example, the stent framework comprised stainless steel with a 10 crest design. This design may result in improved radial strength and greater uniformity after stent expansion as compared with designs having fewer crests. The stent (cobalt chromium) possessed the following additional characteristics: conformal coating with a drug-containing layer of biodegradable polymer (PLGA, 3.5-10 um) with 1.4 ug/mm2 of Sirolimus; 80 um strut thickness; and an electrografted durable/biocompatible base layer (supporting the drug-containing layer) made of PBMA with a thickness of 100 nm-200 nm.

Figure 2:
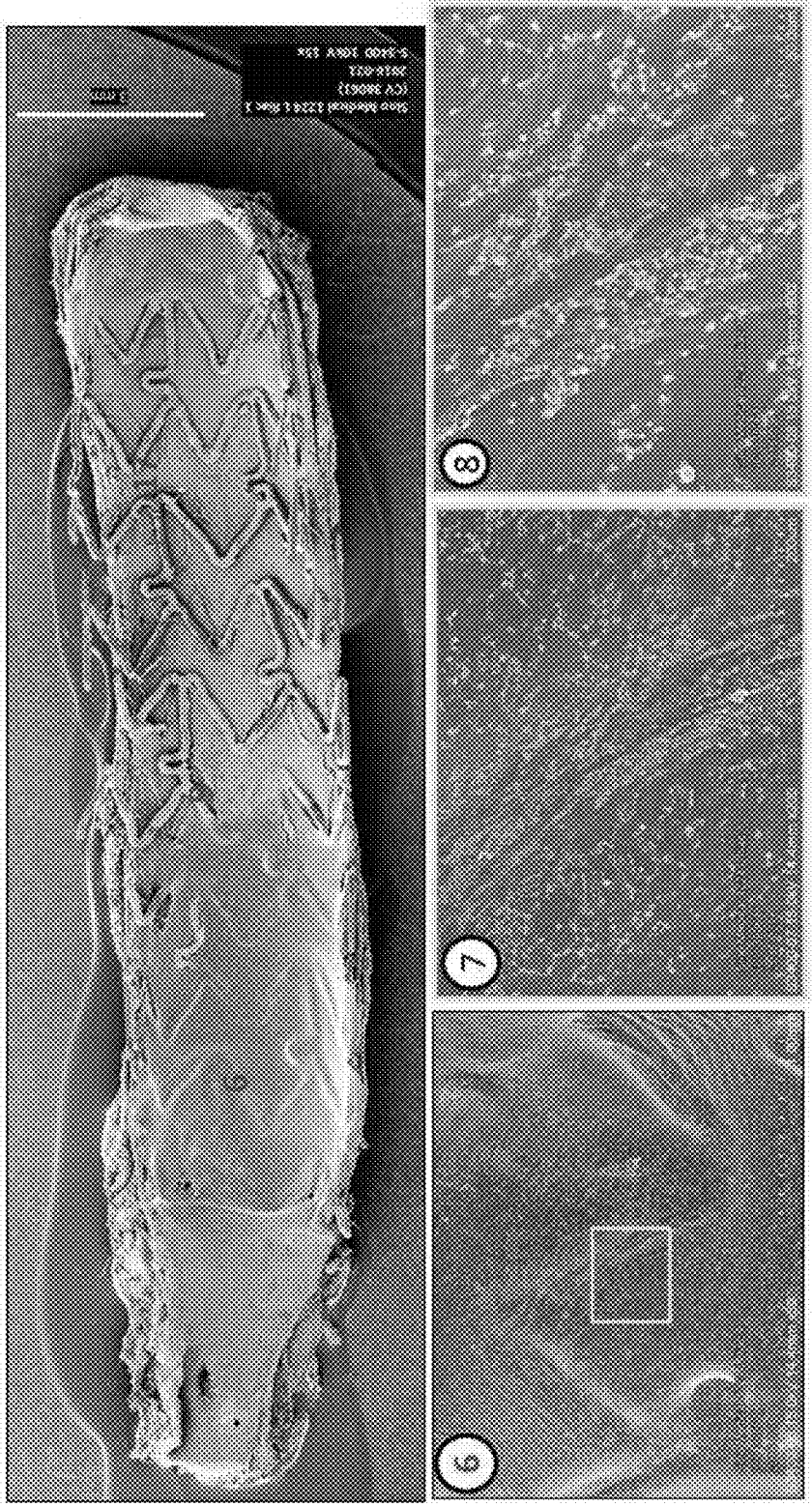
FIG. 2 depicts a Xience Xpedition stent 60 days after implantation imaged using SEM. The SEM images depict partial strut coverage with uncovered areas confined to middle and distal region of the stent. The percentage of endothelial coverage above stent struts is about 50%.
Figure 3:
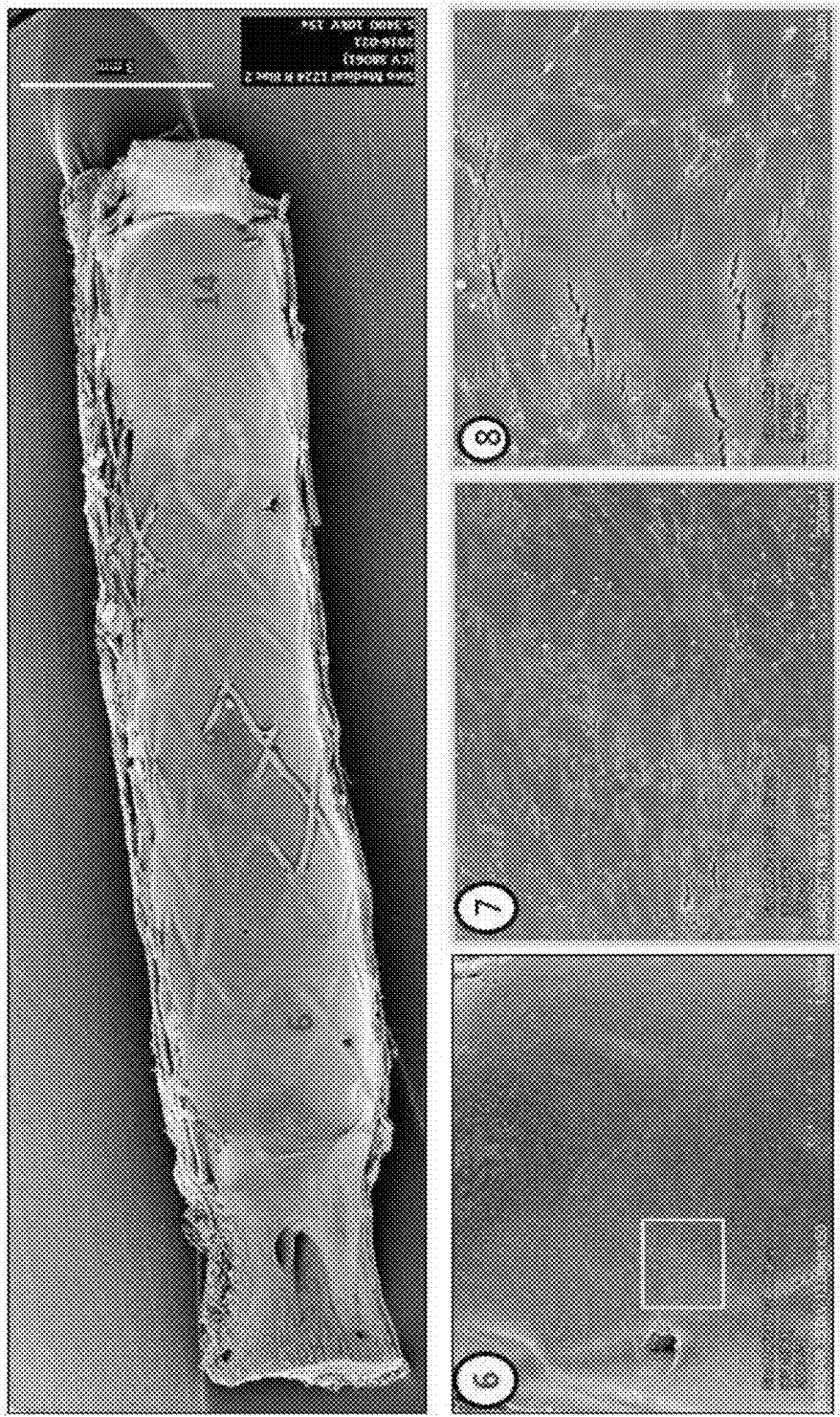
FIG. 3 depicts a drug eluting stent, according to some embodiments of the present disclosure, 60 days after implantation imaged using SEM. The SEM images depict a well-covered stent with few uncovered struts localized to the middle of the stent. The percentage of endothelial coverage above stent struts is about 80%.
Figure 4A:
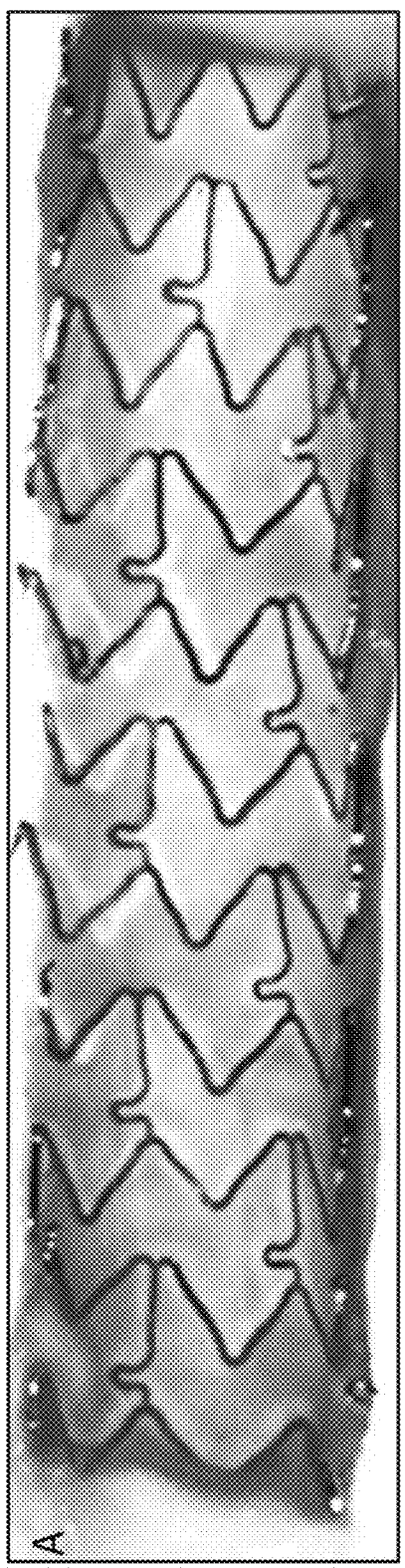
FIG. 4A depicts a Xience Xpedition stent 60 days after implantation imaged using gross images with Evans Blue uptake, in which the positive stained area was 41.8%.
Figure 4B:
FIG. 4B depicts a confocal microscope image of the Xience Xpedition stent of FIG. 4A 60 days after implantation with tiling at 10× objective and with dual immunofluroescent staining of VE-Cadherin (red channel) and P120 (Endothelial p120-catenin) (green channel). The scale bar is 1 mm.
Figure 4C:
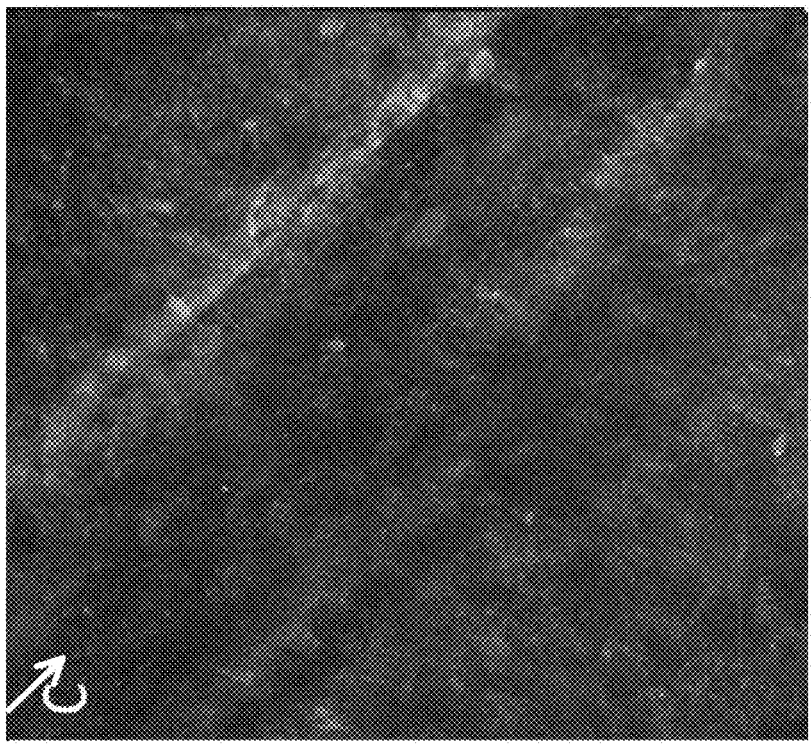
FIG. 4C depicts a confocal microscope image of a region of the Xience Xpedition stent of FIG. 4B 60 days after implantation with 20× objective, where the region had VE-Cadherin poorly expressed at endothelial borders, generally indicating poor barrier function. VE-Cadherin was red channel (555 nm), P120 was green channel (488 nm), and blue channel (405 nm) was DAPI counterstain. The scale bar is 50 μm.
Figure 4D:
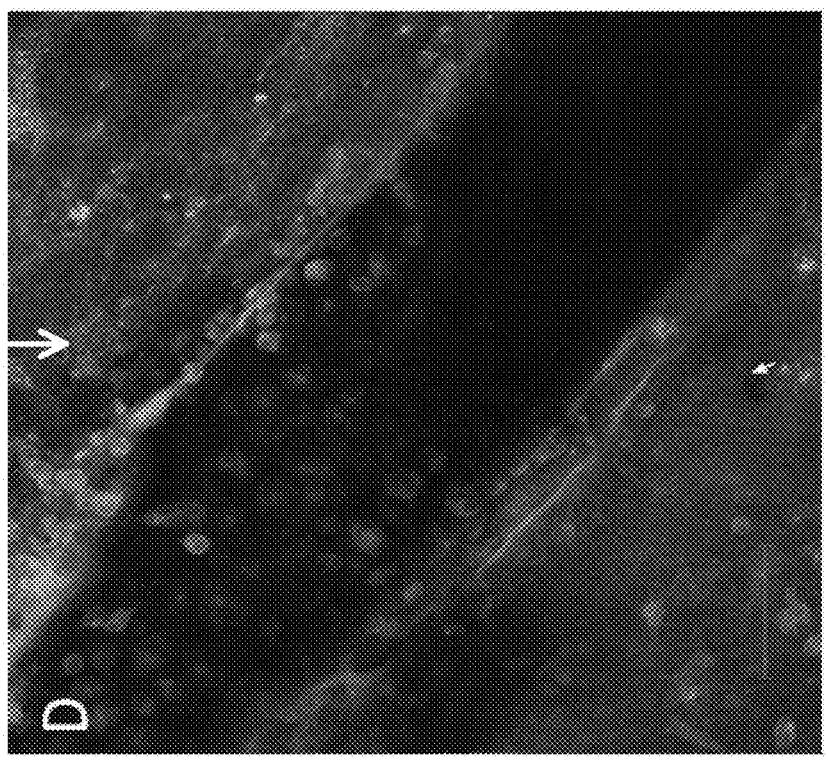
FIG. 4D depicts a confocal microscope image of another region of the Xience Xpedition stent of FIG. 4B with 20× objective, where the region had VE-Cadherin poorly expressed at endothelial borders, generally indicating poor barrier function. VE-Cadherin was red channel (555 nm), P120 was green channel (488 nm), and blue channel (405 nm) was DAPI counterstain. The scale bar is 50 μm. As depicted in FIGS. 4A-4D, endothelial coverage from both markers was 21.2% above the struts; and 21.2% between the struts=21.2%.
Figure 5A:
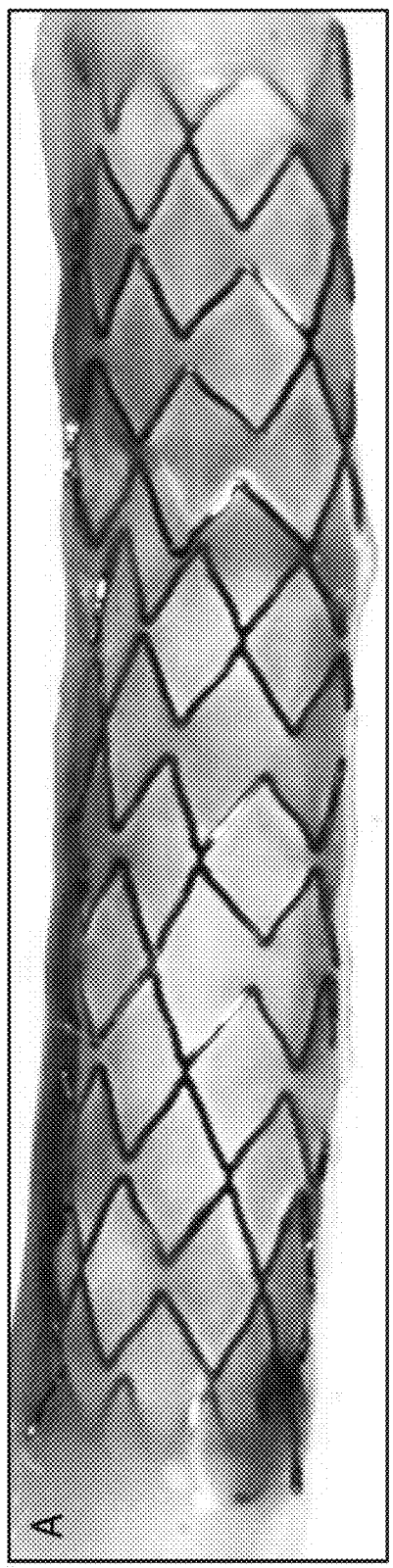
FIG. 5A depicts a drug eluting stent, according to some embodiments of the present disclosure, 60 days after implantation imaged using gross images with Evans Blue uptake, in which the positive stained area was 35.7%.
Figure 5B:
FIG. 5B depicts a confocal microscope image of the drug eluting stent of FIG. 5A 60 days after implantation with tiling at 10× objective and with dual immunofluorescent staining of VE-Cadherin (red channel) and P120 (green channel). The scale bar is 1 mm.
Figure 5C:
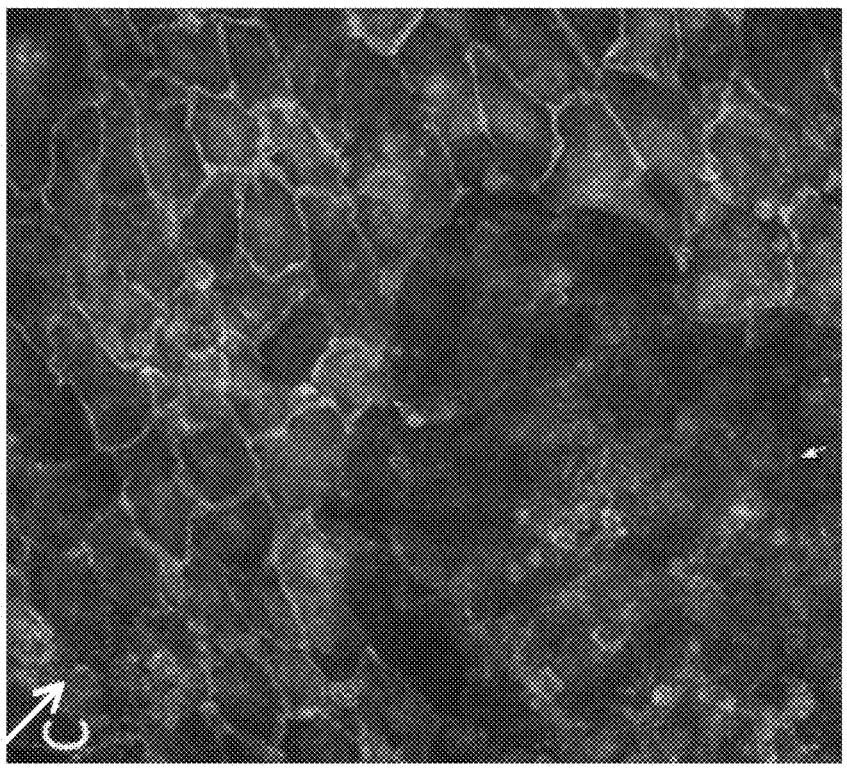
FIG. 5C depicts a confocal microscope image of a region of the drug eluting stent of FIG. 5B 60 days after implantation with 20× objective, where the region had partially endothelial barrier functioned area. VE-Cadherin was red channel (555 nm), P120 was green channel (488 nm), and blue channel (405 nm) was DAPI counterstain. The scale bar is 50 μm.
Figure 5D:
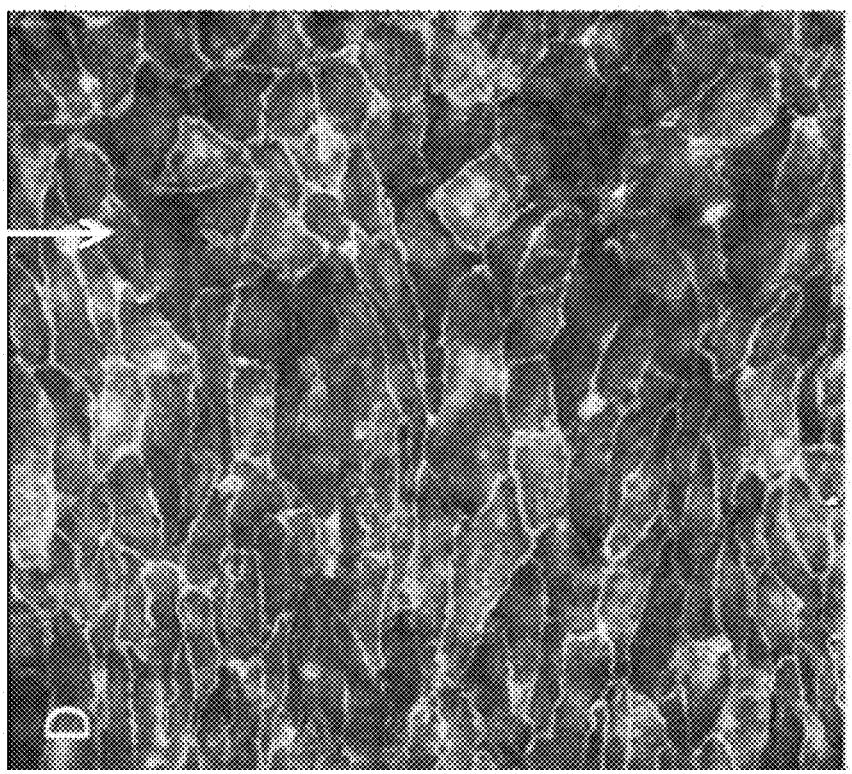
FIG. 5D depicts a confocal microscope image of another region of the drug eluting stent of FIG. 5B 60 days after implantation with 20× objective, where the region had VE-Cadherin poorly expressed at endothelial borders, generally indicating poor barrier function. VE-Cadherin was red channel (555 nm), P120 was green channel (488 nm), and blue channel (405 nm) was DAPI counterstains. The scale bar is 50 μm. As depicted in FIGS. 5A-5D, endothelial coverage from both markers was 36.8% above the struts; and 38.8% between the struts.

A number of stents with these properties were implanted into rabbits. All surgeries were performed using aseptic techniques. Rabbits were placed in a supine position and the hind-legs abducted and externally rotated at the hips with the knees extended. During surgery to stabilize the animal's physiologic homeostasis, animals were maintained on 0.9% Sodium Chloride, USP, intravenous drip at the rate of 10-20 ml/kg/hr and on warm water blanket. The animal's heart rate, blood pressure, body temperature, respiratory rate, $O_2$ saturation, $CO_2$ level, and the concentration Isoflurane was monitored and recorded every 15 minutes. The left and right iliac arteries were injured by balloon endothelial denudation. A 3.0 mm×8 mm standard angioplasty balloon catheter was placed in the distal iliofemoral artery over a guide wire using fluoroscopic guidance and inflated to 8 ATM with 50:50 contrast/saline. The catheter then was withdrawn proximally in its inflated state approximately to the level of the iliac bifurcation. The balloon was deflated, repositioned in the distal iliac, and vessel denudation at 10 ATM then was repeated over the same section of vessel initially denuded. Immediately following balloon denudation, coronary stents (BuMA Supreme, Xience [Xience Xpedition], of BuMA BMS (3.0 mm×15.0 mm) were implanted in the denuded segment of the iliofemoral artery according to the scheduled allocation. The pre-mounted stent/catheter was delivered into the distal iliofemoral artery over a guide wire using fluoroscopic guidance. Stents was deployed at the suggested nominal inflation pressures (10 ATM) at a target balloon to artery ratio of ~1.3 to 1.0 delivered over 30 seconds. Repeat angiography was performed to assess stent placement and patency. Following post-implant angiography, all catheters/sheaths were then withdrawn and surgical wound closed and the animals recovered. For example, as shown in FIG. 3, when a stent according to the present disclosure (Buma Supreme) was implanted in a rabbit for 60 days, the stent exhibited a better endothelial coverage (80%) as compared with the Xience Xpedition depicted in FIG. 2 (50%), as assessed by scanning electron microscopy (SEM).

Moreover, as shown in FIGS. 5A through 5D, after 60 days of implantation in a rabbit, a stent according to the present disclosure exhibited a better functional endothelial coverage (38%) as compared with the Xience Xpedition stent depicted in FIGS. 4A through 4D (21%).

Figure 6:
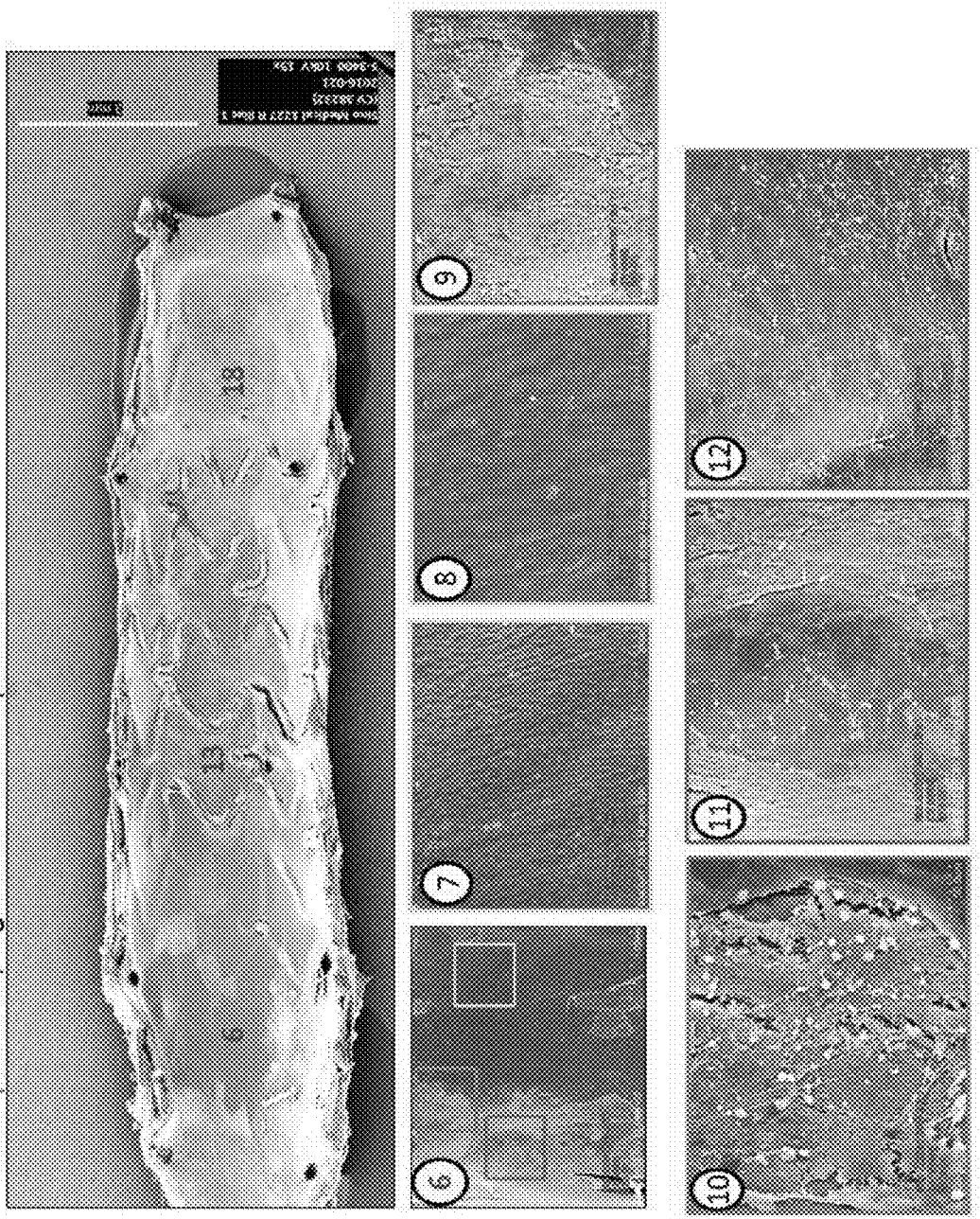
FIG. 6 depicts a Xience Xpedition stent 90 days after implantation imaged using SEM. The SEM images show partial stent coverage with uncovered areas mostly in the middle section. The percentage of endothelial coverage above stent struts is about 70%.
Figure 7:
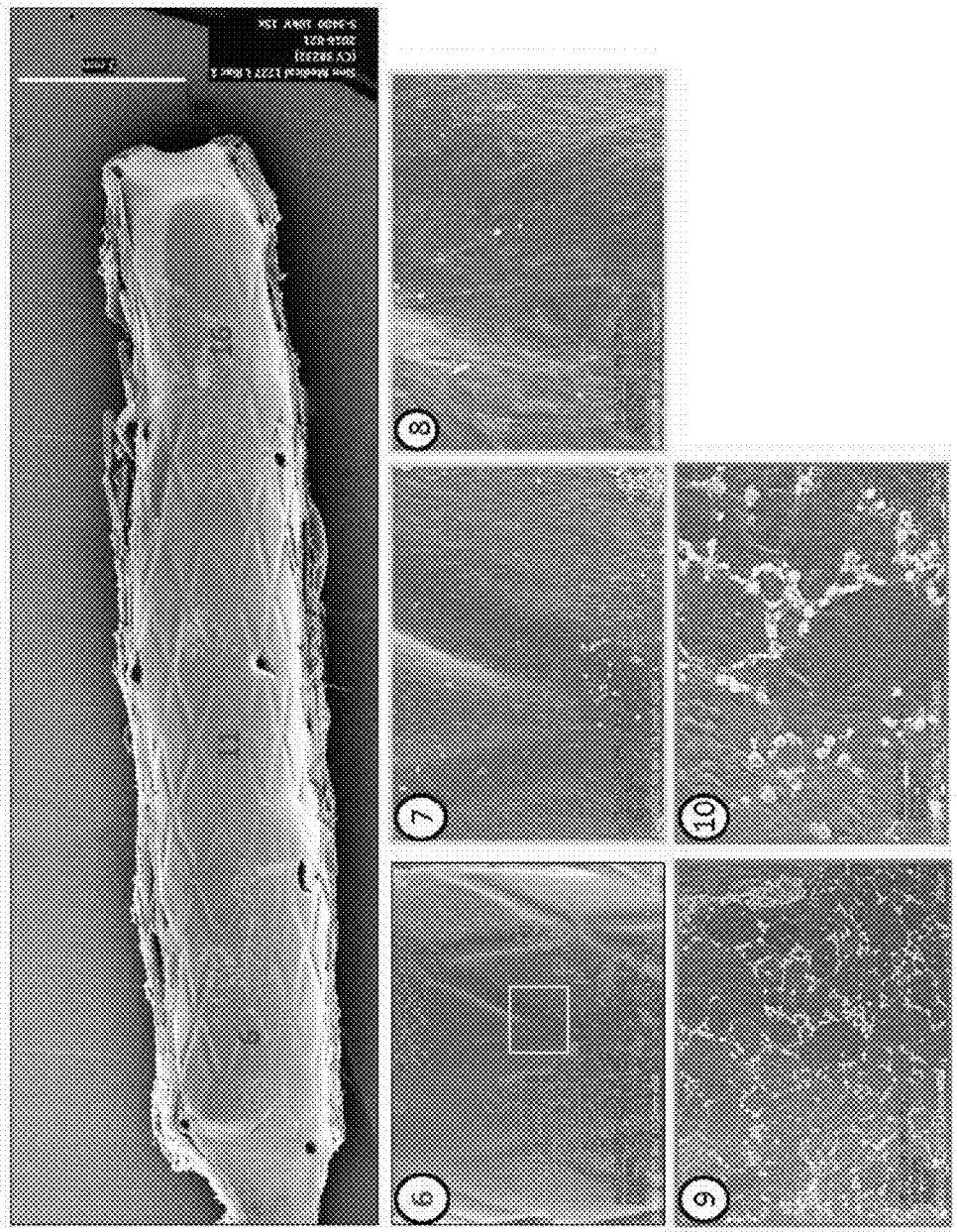
FIG. 7 depicts a drug eluting stent, according to some embodiments of the present disclosure, 90 days after implantation imaged using SEM. The SEM images show complete stent coverage. The percentage of endothelial coverage above stent struts is about 99%.
Figure 8A:
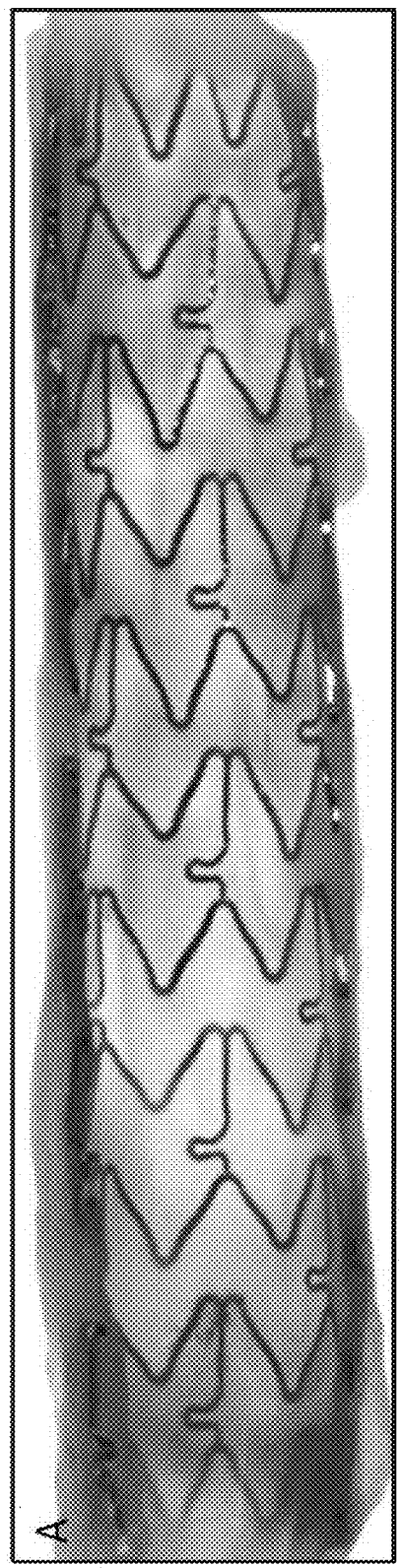
FIG. 8A depicts a Xience Xpedition stent 90 days after implantation using gross images with Evans Blue uptake, in which the positive stained area was 31.8%.
Figure 8B:
FIG. 8B depicts a confocal microscope image of the Xience Xpedition stent of FIG. 8A 90 days after implantation with tiling at 10× objective and with dual immunofluroescent staining of VE-Cadherin (red channel) and P120 (green channel). The scale bar is 1 mm.
Figure 8C:
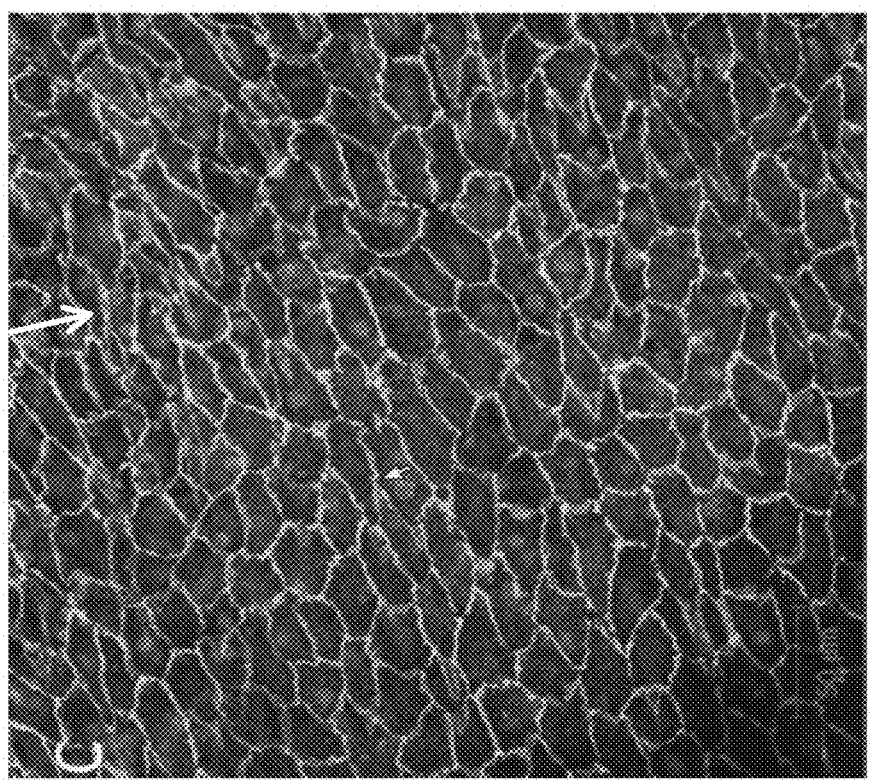
FIG. 8C depicts a confocal microscope image of a region of the Xience Xpedition stent of FIG. 8B 90 days after implantation with 20× objective, where the region had evidence of competent endothelial barrier function (that is, co-localized p120/VE-cadherin). VE-Cadherin was red channel (555 nm), P120 was green channel (488 nm), and blue channel (405 nm) was DAPI counterstain. The scale bar is 50 μm.
Figure 8D:
FIG. 8D depicts a confocal microscope image of another region of the Xience Xpedition stem of FIG. 8B 90 days after implantation with 20× objective, where the region had VE-Cadherin poorly expressed at endothelial borders, generally indicating poor barrier function. VE-Cadherin was red channel (555 nm), P120 was green channel (488 nm), and blue channel (405 nm) was DAPI counterstain. The scale bar is 50 μm. As depicted in FIGS. 8A-8D, endothelial coverage from both markers was 46.8% above the struts; and 46.1% between the struts.

As further shown in FIG. 7, after 90 days of implantation in a rabbit, a stent according to the present disclosure exhibited a better endothelial coverage (99%) as compared with the Xience Xpedition stent depicted in FIG. 6 (70%).

Figure 9A:
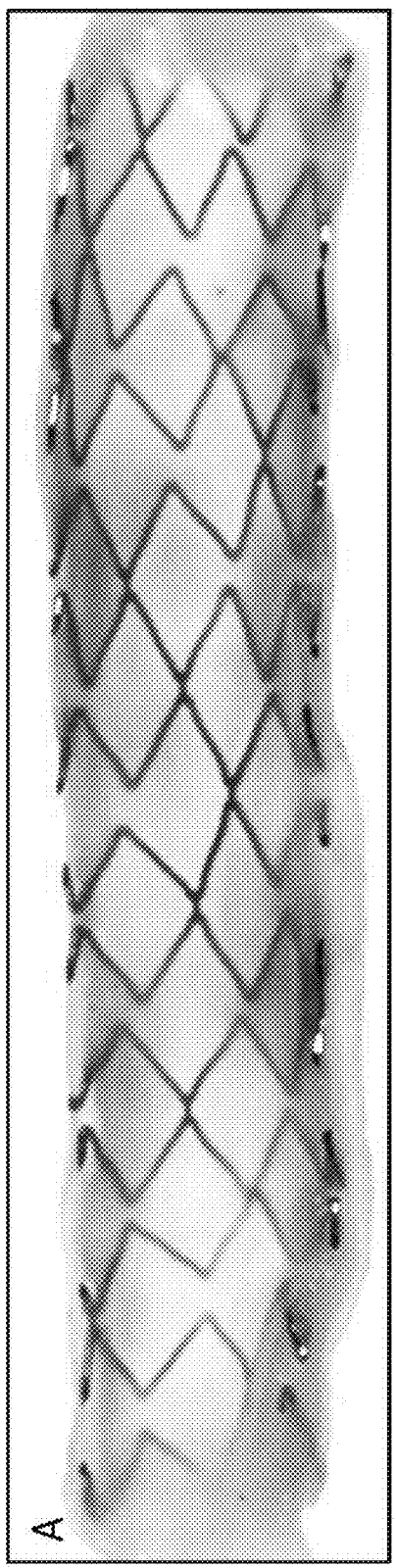
FIG. 9A depicts a drug eluting stent, according to some embodiments of the present disclosure, 90 days after implantation imaged using gross images with Evans Blue uptake, in which the positive stained area was 6.4%.
Figure 9B:
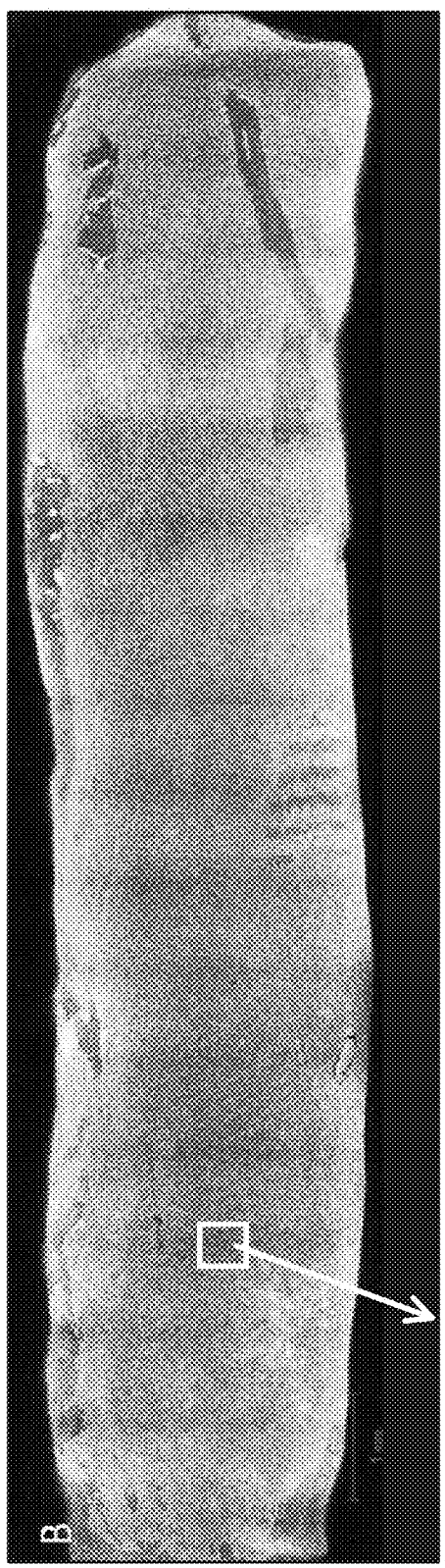
FIG. 9B depicts a confocal microscope image of the drug eluting stent of FIG. 9A 90 days after implantation with tiling at 10× objective and with dual immunofluroescent staining of VE-Cadherin (red channel) and P120 (green channel). The scale bar is 1 mm.
Figure 9C:
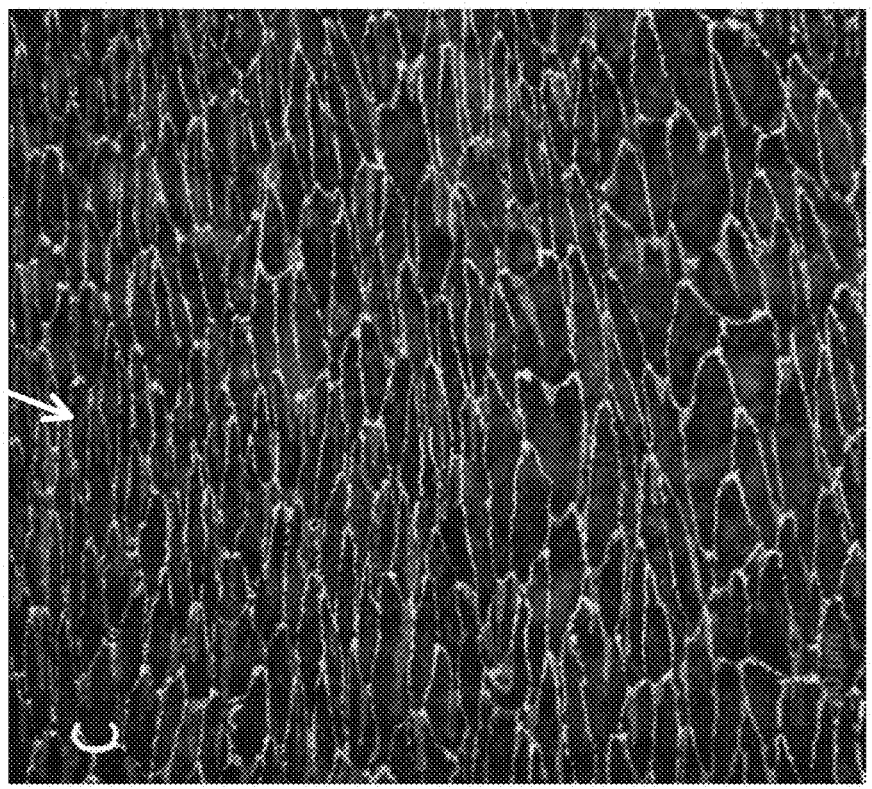
FIG. 9C depicts a confocal microscope image of a region of the drug eluting stent of FIG. 9B 90 days after implantation with 20× objective, where the region had evidence of competent endothelial barrier function (that is, co-localized p120/VE-cadherin). VE-Cadherin was red channel (555 nm), P120 was green channel (488 nm), and blue channel (405 nm) was DAPI counterstain. The scale bar is 50 μm.

Finally, as shown in FIGS. 9A through 9C, after 90 days of implantation in a rabbit, a stent according to the present disclosure exhibited a better functional endothelial coverage (100%) as compared with the Xience Xpedition stent depicted in FIGS. 8A through 8D (46%).

A second set of experiments was prepared according to this example method with the following stent framework structure:

The stent (BuMA Supreme) was coated by e spray coating process described above with a conformal coating of biodegradable polymer (PLGA). The strut thickness was 80 um and the stent was made of Cobalt-chromium alloy. The eG-layer was made of PBMA (100 nm-200 nm) and the drug containing layer of PLGA (3.5 to 10 um) with 1.4 ug/mm2 of sirolimus.

Similarly to the previous experiments, the stents were implanted into rabbits and their endothelialization was studied over time (e.g., 45 and 90 days) using Evan's Blue and VE-Cadherin/P120 colocalization. The results are exemplified in FIGS. 12A through 12D for 45 days Evan's Blue; FIGS. 13A through 13D for VE-Cadhering/P120 colocalization at 45 days; FIGS. 14A through 14D for 90 days Evan's Blue; and FIGS. 5A through 15D for VE-Cadhering/P120 colocalization at 90 days. As shown in these figures, stents according to the disclosure (BuMA Supreme stents) have a larger percentage of endothelial cell colocalization of VE-Cadhering/P120 (i.e., the endothelium is better and more functional) than other drug eluting stents tested not according to the disclosure. In addition, the permissibility of the endothelial cell layer covering the stents of the disclosure (BuMA Supreme stents), as assessed by Evan's Blue staining, is lower than that of other tested drug eluting stents not according to the disclosure, indicating that the endothelium is more functional in the BuMA Supreme stents.

It is also envisioned that the stent framework may comprise a wave design with an alternating pattern of two-three-two-three link poles spirally arranged in the axial direction. This design may improve bendability of the stent and may result in better fitting to the vessel after stent expansion. In some embodiments, both ends of the stent may have two link poles or three link poles in accordance with the two-three-two-three pattern. In other embodiments, both ends of the stent may have four link poles, which may increase axial strength of the stent. Dimensions of this example design may include, for example, a pole width of 90 μm, and a crown width of 100 μm. In having a crown width greater than the pole width, the stent may have grater radial strength and have a reduced crossing profile with the vessel after stent expansion. In addition, dimensions of this example design may include a wall thickness of 80 μm or 90 μm.

C. Human Clinical Trials

Human clinical trials were performed with stents made of stainless steel (316L) (BUMA stents). The stents were designed to either have an OD: 1.6 and 6 crests (first design) or an OD of 1.8 and 9 crests (second design). The pole width of the first design was 110 μm and of the second design 90 μm. The wall thickness of the first design was 100 μm and of the second design was 110 μm. These stents were coated by the spray coating method described above.

A clinical trial titled "A prospective randomized controlled 3 and 12 months OCT study to evaluate the endothelial healing between a novel sirolimus eluting stent BUMA and an everolimus eluting stent XIENCE V" was done. The BUMA stent was designed with a 30-day drug release time frame and a 60-day coating/drug-containing layer bio-degradable time frame and fabricated according to Example 1 above. On the other hand, a Xience V stent is designed with a 120-day drug release time frame, and the coating is bio-stable. Twenty patients were enrolled into the study. The BUMA and XIENCE V stents were overlapped implanted at the same lesion in the same vessel of the same patient. The study showed that the struts of both stents were well-covered at 3 months and 12 months OCT follow-up. However, the struts of the BUMA stent had significantly coverage compared to the struts of the XIENCE V stent at 12 months (99.2% BUMA vs. 98.2% XIENCE V with P<0.001). Moreover, the struts of the BUMA stent had a thicker neointimal hyperplasia thickness and larger neointimal area than the struts of the XIENCE V stent (0.15±0.10 mm BUMA vs. 0.12±0.56 mm XIENCE V with P<0.001). As explained above, a thickness below a first threshold (e.g., 0.1 mm) may be indicative of an insufficient number of endothelial cells while a thickness above a second, higher threshold (e.g., 0.50 mm) may be indicative of a ratio of smooth cells to endothelial cells that is too high. In addition, the BUMA stent had a more uniform strut coverage compared to the XIENCE V stent. The study shows that the BUMA stent had better long-term safety than the XIENCE V stent.

Another clinical trial named "Biodegradable Polymer-Based Sirolimus-Eluting Stents With Differing Elution and Absorption Kinetics" was done. The BUMA stent was designed with a 30-day drug release time frame and a 60-day coating bio-degradable (disappearance/dissolution/dissipation of the drug-containing layer) time frame and fabricated according to Example 1 above. The EXCEL stent was designed with a 180-day drug release time frame and a 180-to-270-day coating bio-degradable time frame. Two thousand three hundred forty-eight patients were enrolled into the study. The BUMA stent exhibited a lower incidence of stent thrombosis than the EXCEL stent. In particular, the 1-year rate of stent thrombosis was lower with the BUMA stent than the EXCEL stent, a difference that was evidenced within the first month after implantation.

Another clinical trial named "PIONEER-II Study" compared 1-month optical coherence tomography (OCT) results between a BUMA stent and a Xience V stent. The BUMA stent was designed with a 30-day drug release time frame and a 60-day bio-degradable time frame for the drug containing layer and fabricated according to Example 1 above. The Xience V stent was designed with a 120-day drug release time frame, and the coating was bio-stable. Fifteen patients were enrolled into the study. The study showed that struts neointimal coverage at 1-month by OCT follow-up for the BUMA stent exhibited better coverage compared to the Xience V stent (83.8% BUMA vs. 73.0%, Xience V with P<0.001).

Example 2

Dispense Coating Process

A. Process

In some embodiments, the drug-containing layer (3) may be formed using a dispense coating process to dispose a polymer coating on the stent framework (or on a polymer-coated stent, e.g., a stent coated in the electro-grated coating described below). In one example, after drying, a 20 millimeter stent was dispense coated with biodegradable polyester (polylactide, p-PLA) containing Sirolimus. The copolymer (5% w/v) was dissolved in chloroform. Sirolimus was then dissolved in the chloroform/polymer mixture to obtain a final ratio 1:5 Sirolimus/polymer of (1/5). A micro dispenser was run along with the stent struts and links and dispensed the mixture onto the abluminal side (8) of the stent by a micro dispenser using the following parameters:

| Dispenser parameter | |
|---|---|
| Dispensing flow (µL/s) | 10 |
| Dispensing volume (µL/s) | 145 |
| Pressure (bar) | 0.1 |
| Dispenser run speed (mm/s) | 0.5 |
| Dispenser/stent distance (mm) | 1.1 |
| Number of dispenser run | 10 |

The coating was applied to the abluminal side (8) of the stent only. Drying at 40° C. was performed in a vacuum oven. In this example, the coating on the stent weighs 500±50 µg, and the coating thickness was about 9-12 µm. Moreover, in this example, the drug loading was 125±12 µg.

The Electro-Grafted Coating (eG Coating)

In some embodiments, the biocompatible base layer (5) may further comprise/be made by an electro-grafted coating. More details about the process of electrografting coating of a stent are available in the art, including, for example, U.S. patent application Ser. No. 13/850,679 (published as 2014/0296967 A1), U.S. patent application Ser. No. 11/808,926 (published as 2007/0288088 A1), and U.S. Provisional Patent Application No. 60/812,990, all of which incorporated by reference herein.

The electro-grafted layer may function as an adhesion primer for the drug-containing layer (3) (e.g., during manufacturing, crimping and/or stenting). The electro-grafted primer coating may be uniform. This layer may have a thickness between 10 nm and 1.0 micron, e.g., between 10 nm and 0.5 micron or between 100 nm and 300 nm. Such a thickness may ensure that the coating does not crack. Electro-grafted layers are often capable of preventing the cracking and delamination of biodegradable polymer layers, and often exhibit equal, if not better recolonization, than stainless steel BMS. Furthermore, the use of an electro-grafted layer having a thickness of at least about a few tens or of a hundred nanometers may secure a good reinforcement of adhesion of the drug-containing layer (3) on account of interdigitation between the two polymeric layers. Accordingly, the choice of the nature of the electro-grafted polymer may be based upon the nature of the release matrix polymer, which itself may be chosen on the basis of the loading and kinetics of the desired drug release. In some embodiments, the electro-grafted polymer and the release matrix polymers may be at least partially miscible in order to constitute a good interface. This is the case when, for example, the two polymers have close solubility or Hildebrand parameters, or when a solvent of one of the polymers is at least a good swellant to the other.

In general, the electro-grafted polymer may be chosen from polymers known to be biocompatible. For example, the polymers may be chosen from those obtained via propagation chain reaction, such as vinylics, epoxides, cyclic monomers undergoing ring opening polymerization, or the like. Accordingly, poly-Butyl MethAcrylate (p-BuMA), poly-Methyl MethAcrylate (PMMA), or poly-EpsilonCaproLactone (p-ECL) may be used. Alternatively or concurrently, Poly-HydroxyEthyl MethAcrylate (p-HEMA) may also be used.

The electro-grafted layer, (e.g., a p-BuMA layer) may further have a passivating behaviour and may block the release of heavy metal ions (e.g., in the blood flow or in the artery walls) from the stent framework. Said heavy metal ions may contribute to the initial inflammation caused by the introduction of the metal stent in the blood, which may provoke the partial oxidization of any metal until Nernst equilibrium is reached. In particular, the thickness of the artery walls of the electro-grafted layer and biodegradable (with no drug) branch are usually smaller than those of the bare metal stent branch, evidencing less granuloma, i.e., less inflammation.

In one embodiment, the electro-grafted layer may be biodegradable, and thus may disappear from the surface of the stent after the drug-containing layer has also disappeared.

The electro-grafted layer may have a non-thrombotic (or thromboresistant) effect and a pro-healing effect (e.g., promoting the proliferation and adhesion of active ECs). If the ECs start proliferating on the top of the drug-containing layer (e.g., before it has fully disappeared), hydrolysis of the biodegradable polymers may nevertheless continue underneath, and the ECs may eventually contact the electro-grafted layer. Such a pro-healing effect may be similar to that of the stent framework if the electro-grafted layer is biodegradable itself. The pro-healing effect may be greater with a biostable electro-grafted layer that secures proper recolonization by ECs in the longer term.

In some embodiments, the electro-grafted layer may additionally be made of anti-fouling materials.

The polymers which may be used as electro-grafted coating mention including, but are not limited to, vinyl polymers, such as polymers of acrylonitrile, of methacrylonitrile, of methyl methacrylate, of ethyl methacrylate, of propyl methacrylate, of butyl methacrylate, of hydroxyethylmethacrylate, of hydroxylpropylmethacrylate, of cyanoacrylates, of acrylic acid, of methacrylic acid, of styrene and of its derivatives, of N-vinylpyrrolidone, of vinyl halides and polyacrylamides, of isoprene, of ethylene, of propylene, of ethylene oxide, of molecules containing a cleavable ring such as lactones and, in particular, ε-caprolactone, of lactides, of glycolic acid, of ethylene glycol, as well as polyamides, polyurethanes, poly(orthoesters), polyaspartates, or the like.

In some embodiments, the electro-grafted coating may be a vinylic polymer or copolymer, such as poly butyl methacrylate (poly-BUMA), poly hydroxyethylmethacrylate (poly-HEMA), poly 2-methacryloyloxyethyl phosphorylcholine/butyl methacrylate (poly-MPC/BUMA), poly-methacryloyloxyethyl phosphorylcholine/dodecyl methacrylate/trimethylsilylpropylmethacrylate (poly-MPC/DMA/TMSPMA), or the like. In certain aspects, the electro-grafted coating may be a biodegradable polymer, such as a poly-caprolactone, a polylactide (PLA) or a polyglycolactide (PLGA).

Adhesion Between the Electro-Grafted Coating and the Biodegradable Layer (Drug-Containing Layer or Topcoat Layer)

The drug-containing layer may adhere onto the electro-grafted layer by forming a chemical bond with the electro-grafted polymer; inserting, in the electro-grafted polymer, chemical precursors of the drug-containing layer, in order to provoke its formation inside the electro-grafted polymer film; forcing the interpenetration of pre-formed biodegradable polymer inside the electro-grafted layer by interdigitation; etc. Interdigitation generally relates to the fact that the polymeric chains of the the biodegradable polymer may "creep" or "reptate" inside the electro-grafted layer and may form at least one "loop" inside the electro-grafted layer. For a polymer, one "loop" may refer to the typical size of a chain when in a random configuration and may be evaluated using the radius of gyration of the polymer. Generally, the radius of gyration of a polymer is smaller than 100 nm, suggesting that, to enable improved adhesion, electro-grafted layers may be be thicker than this threshold value to be capable of hosting at least one loop of the polymer(s) of the drug-containing layer.

In embodiments using interdigitation, the electro-grafted layer may be thicker than about 100 nm, may have a wettability (e.g., hydrophobic/hydrophilic) identical to that of the polymer(s) of the drug-containing layer, may have a glass transition temperature smaller than that of the polymer(s) of the drug-containing layer, and/or may be at least partially swollen by a solvent of the polymer(s) of the drug-containing layer or by a solvent containing a dispersion of the polymers) of the drug-containing layer.

In some embodiments, interdigitation may be caused by spreading a solution containing the drug-containing layer (and optionally the drug) over a stent framework coated with an electro-grafted layer. For example, the drug-containing layer may comprise PLGA may be dissolved in dichloroethane, dichloromethane, chloroform, or the like, optionally with a hydrophobic drugs such as Sirolimus, Paclitaxel, ABT-578, or the like. In such an example, the electro-grafted layer may comprise p-BuMA.

In some embodiments, this spreading may be performed by dipping or by spraying. In embodiments where spraying is used, a nozzle spraying the above solution may face the stent framework, which may rotate in order to present all outside surfaces to the spray. In certain aspects, the solution to be sprayed may have a low viscosity (e.g., <1 cP, the viscosity of pure chloroform being about 0.58 cP), the nozzle may be at short distance from the rotating stent, and the pressure of the inert vector gas (e.g., nitrogen, argon, compressed air, or the like) in the nozzle may be less than 1 bar. These conditions may lead to the nebulization of the liquid into small droplets of liquid, which may travel in the spraying chamber atmosphere to hit the surface of the electro-grafted layer of the stent. In embodiments where the electro-grafted polymer layer and the spray solution have the same wettability, the droplet may exhibit a very low contact angle, and the collection of droplets on the surface may therefore be filmogenic. Such a spray system may enable the manufacturing of coated stents with very little webbing in between the struts.

The relative movement of the nozzle with respect to the stent may enable the deposition of a uniform and/or relatively thin (e.g., <1 μm) layer in a single shot. The rotation and/or air renewal may enable the evaporation of the solvent, leaving the polymer layer (optionally including the drug) on the surface. A second layer may then be sprayed on the first one and so on, in order to reach a desired thickness. In embodiments where several sprays are used to reach the desired thickness, the "low pressure" spray system may be implemented in batches, in which several stents rotate in parallel with one nozzle spraying over each and every stent sequentially, therefore enabling the other stents to evaporate while another one is being sprayed.

In addition to these embodiments, the manufacturing process can comprise any of the methods of manufacturing disclosed in US20070288088 A1, which is incorporated herein by reference.

The described embodiments are to be considered in all respects only as illustrative and not as restrictive. The scope of the present disclosure is, therefore, indicated by the appended claims rather than by the foregoing description.

All changes which come within the meaning and range of the equivalence of the claims are to be embraced within their scope.

What is claimed is:

1. A method of fabricating a drug eluting stent, the method comprising:
   providing a stent framework having a luminal surface, an abluminal surface, and a lateral surface; and
   coating the surfaces of the stent framework with at least a drug-containing layer comprising at least one polymer mixed with at least one drug, wherein the thickness of the coating on the abluminal surface of the stent is higher than the thickness of the coating in the luminal surface of the stent, wherein the stent further comprises an electro-grafted coating disposed on the stent framework underneath the drug-containing layer, wherein the electro-grafted coating has a thickness between 10 nm and 0.5 micrometers, and wherein said drug-containing layer and said electro-grafted polymeric layer are interpenetrated, forming an interdigitated interface without chemical bonding or layering.

2. The method according to claim 1, wherein the drug-containing layer comprises polylactide-co-glycolide 50/50 (PLGA), or a derivative thereof, and wherein the electro-grafted coating comprises poly-Butyl MethAcrylate (p-BuMA).

3. The method according to claim 1, wherein the drug-containing layer comprises a biodegradable polymer, copolymer, and/or block polymer.

4. The method of claim 1, wherein the drug is selected from a group consisting of sirolimus, paclitaxel, ABT-578, everolimus, tacrolimus, and their derivatives or analogs.

5. The method of claim 1, wherein the drug is a bioactive agent selected from the group consisting of an antisense agent, an antineoplastic agent, an antiproliferative agent, an antithrombogenic agent, an anticoagulant, an antiplatelet agent, an antibiotic, an anti-inflammatory agent, a gene therapy agent, a therapeutic substance, an organic drug, a pharmaceutical compound, a recombinant DNA product, a recombinant RNA product, a collagen, a collagenic derivative, a protein, a protein analog, a saccharide, and a saccharide derivative.

6. The method of claim 1, wherein the electro-grafted coating is made from a monomer chosen from the group consisting of vinylics, epoxides and cyclic monomers undergoing ring opening polymerisation and aryl diazonium salts.

7. The method of claim 1, wherein the stent framework comprises a material selected from the group consisting of stainless steel, nitinol, tantalum, cobalt-chromium MP35N or MP20N alloys, platinum, titanium, a suitable biocompatible alloy, a suitable biocompatible material, and a combination thereof.

8. The method of claim 1, wherein the electro-grafted coating has a thickness between 100 nm and 300 nm.

* * * * *